United States Patent [19]

Mix et al.

[11] Patent Number: 5,236,423
[45] Date of Patent: Aug. 17, 1993

[54] FACILITATING ENDOSCOPY

[75] Inventors: Thomas W. Mix, Wellesley; Ernesto E. Blanco, Belmont; Norman Rosskothen, Canton, all of Mass.; Maria L. Hernandez, Lake Zurich, Ill.; Gordon C. Vineyard, Chestnut Hill; Liem T. Vu, Waltham, both of Mass.

[73] Assignee: EndoMed Corporation, Wellesley, Mass.

[21] Appl. No.: 895,193

[22] Filed: Jun. 5, 1992

Related U.S. Application Data

[63] Continuation of Ser. No. 536,205, Jun. 11, 1990, abandoned, which is a continuation-in-part of Ser. No. 284,067, Dec. 13, 1988, abandoned.

[51] Int. Cl.$^5$ .............................................. A61M 5/00
[52] U.S. Cl. ......................................... 604/271; 128/4
[58] Field of Search ................... 604/271, 265; 128/4, 128/156; 156/230, 238, 247, 249, 289

[56] References Cited

U.S. PATENT DOCUMENTS

| | | | |
|---|---|---|---|
| 2,733,180 | 1/1956 | Pinto | 156/247 |
| 3,258,513 | 6/1966 | Berry et al. | 156/247 |
| 3,525,329 | 8/1970 | Zeimer et al. | |
| 3,547,753 | 12/1970 | Sutton | 156/230 |
| 3,589,356 | 6/1971 | Silverman | |
| 3,892,575 | 7/1975 | Watts et al. | 96/84 |
| 3,911,927 | 10/1975 | Rich et al. | |
| 3,982,544 | 9/1976 | Dyck | 604/271 |
| 4,055,682 | 10/1977 | Merrill | 427/2 |
| 4,077,610 | 3/1978 | Masuda | 604/271 |
| 4,100,309 | 7/1978 | Micklus et al. | |
| 4,109,659 | 8/1978 | Sheridan | |
| 4,119,094 | 10/1978 | Micklus et al. | |
| 4,271,839 | 6/1981 | Fogerty et al. | |
| 4,314,814 | 2/1982 | Deroode | 156/238 |
| 4,321,915 | 3/1982 | Leighton et al. | |
| 4,437,857 | 3/1984 | Goldstein et al. | |
| 4,479,497 | 10/1984 | Fogarty et al. | |
| 4,493,711 | 1/1985 | Chin et al. | |
| 4,503,111 | 3/1985 | Jaeger et al. | 428/195 |
| 4,530,698 | 7/1985 | Goldstein et al. | |
| 4,554,317 | 11/1985 | Behar et al. | 128/156 |
| 4,585,666 | 4/1986 | Lambert | 427/2 |
| 4,589,873 | 5/1986 | Schwartz et al. | 604/265 |
| 4,604,094 | 8/1986 | Shook et al. | |
| 4,606,347 | 8/1986 | Fogarty et al. | |
| 4,615,331 | 10/1986 | Kramann | |
| 4,630,609 | 12/1986 | Chin | |
| 4,666,437 | 5/1987 | Lambert | 604/265 |
| 4,769,013 | 9/1988 | Lorenz et al. | 604/265 |
| 4,943,460 | 7/1990 | Markle et al. | 604/265 |
| 4,980,231 | 12/1990 | Baker et al. | 604/265 |
| 5,045,070 | 9/1991 | Grodecki et al. | 604/271 |

FOREIGN PATENT DOCUMENTS 2823025 8/1970 Fed. Rep. of Germany.

OTHER PUBLICATIONS

H. Zeimer et al.; Toposcopy, Frictionless Method of Entering Body Cavities and Tracts; Jul. 15, 1986; New York State Journal of Medicine; pp. 1925–1930.

S. R. Goldstein, et al.; A Miniature Toposcopic Catheter Suitable for Small Diameter Tortuous Blood Vessels; Aug. 1980; Transactions of the ASME; vol. 102; pp. 221–229.

J. L. Doppman et al.; The Toposcopic Catheter: A Design for Maneuvering Through Tortuous Vessels; Sep. 1979; Radiology; vol. 132; pp. 735–737.

D. R. Shook et al.; Everting (Toposcopic) Catheter for Broad Clinical Application; May 1986; Transaction of ASME; vol. 108; pp. 168–174.

D. R. Shook; The Ins and Outs of Toposcopy and The Everting Catheter; Jul. 1987; Soma: Engineering for the Human Body; Jul. 1987; pp. 22–27.

S. B. Benjamin et al.; The toposcopic through–lumen everting catheter to facilitate dilatation of severe strictures of the gastrointestinal tract; Gastrointestinal Endoscopy; vol. 32, No. 1; 1986.

J. P. Alspaugh et al.; Everting Balloon Catheter in the Biliary Tree: A Technical CardioVascular and Interventional Radiology; vol. 9; 1986; pp. 164–166.

S. R. Goldstein et al.; The toposcopic catheter and the fiberoptic pH probe–two . . . Gastrointestinal Endoscopy; vol. 29, No. 3.

Primary Examiner—Ralph Lewis
Attorney, Agent, or Firm—Fish & Richardson

[57] ABSTRACT

One aspect is a method for inserting an instrument into the gastrointestinal tract of a mammal, by emplacing at least a portion of a flexible liner to form within the intestine an inner tube within an outer tube, the inner tube defining a lumen lying within the intestine and having a distal end accessible via the anal opening from outside the body of the mammal, and thereafter passing the instrument into the lumen via its distal end. Another aspect is the combination of an elongate evertible liner, a liner support chamber having a proximal port and a distal port, the liner having its two ends attached respectively at the ports, and a pressurizer for increasing the pressure within the chamber to cause the liner to be everted, the liner comprising a material characterized by having a wall thickness to diameter ratio and a zero strain elasticity modulus whose product is less than 4.0 lb/inch$^2$, preferably less than 1.0 lb/inch$^2$, and a wall thickness to diameter ratio and a 100% strain modulus of elasticity whose product is greater than 0.5 lb/inch$^2$, preferably greater than 2.0 lb/inch$^2$. In another aspect, a layer of lubricous material, such as polyvinylpyrrolidone (PVP), is directly bonded to a surface of a layer of elastomeric material (such as polyurethane) without the use of adhesive materials between the layers. The resultant PVP-coated sheet is formed into the flexible liner. Yet another aspect is several devices for emplacing the liner in the intestine.

26 Claims, 27 Drawing Sheets

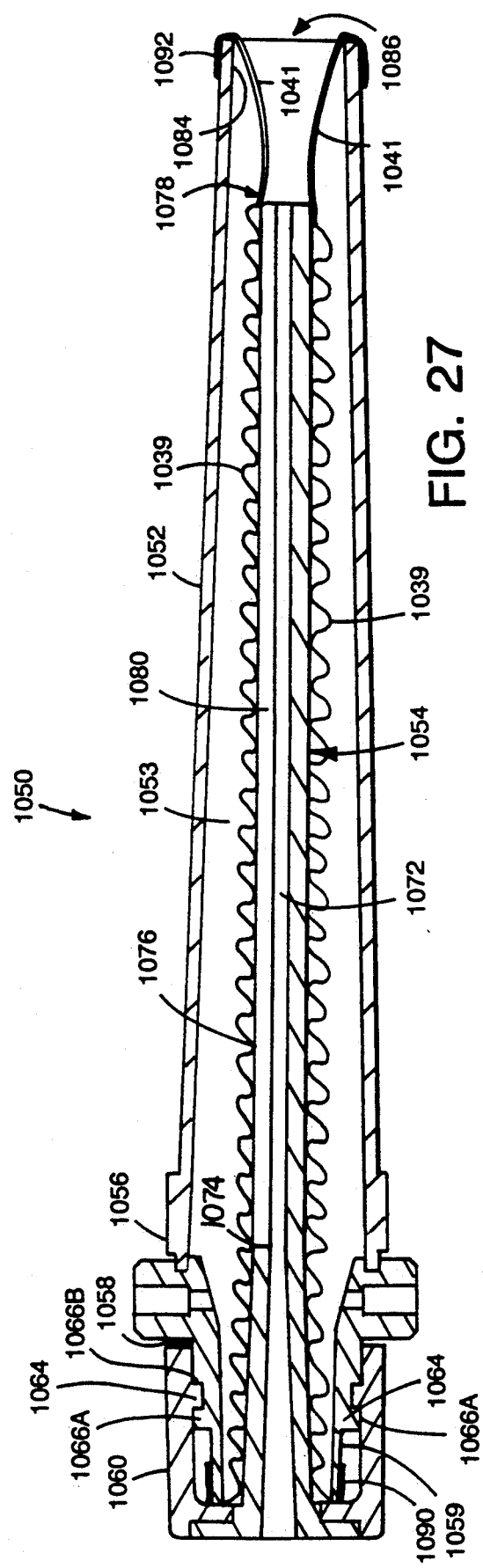
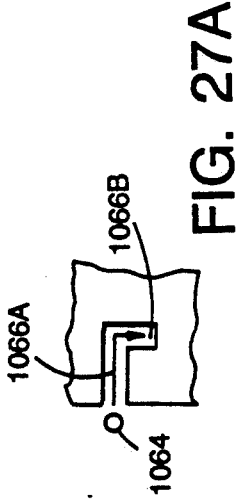
FIG. 27
FIG. 27A

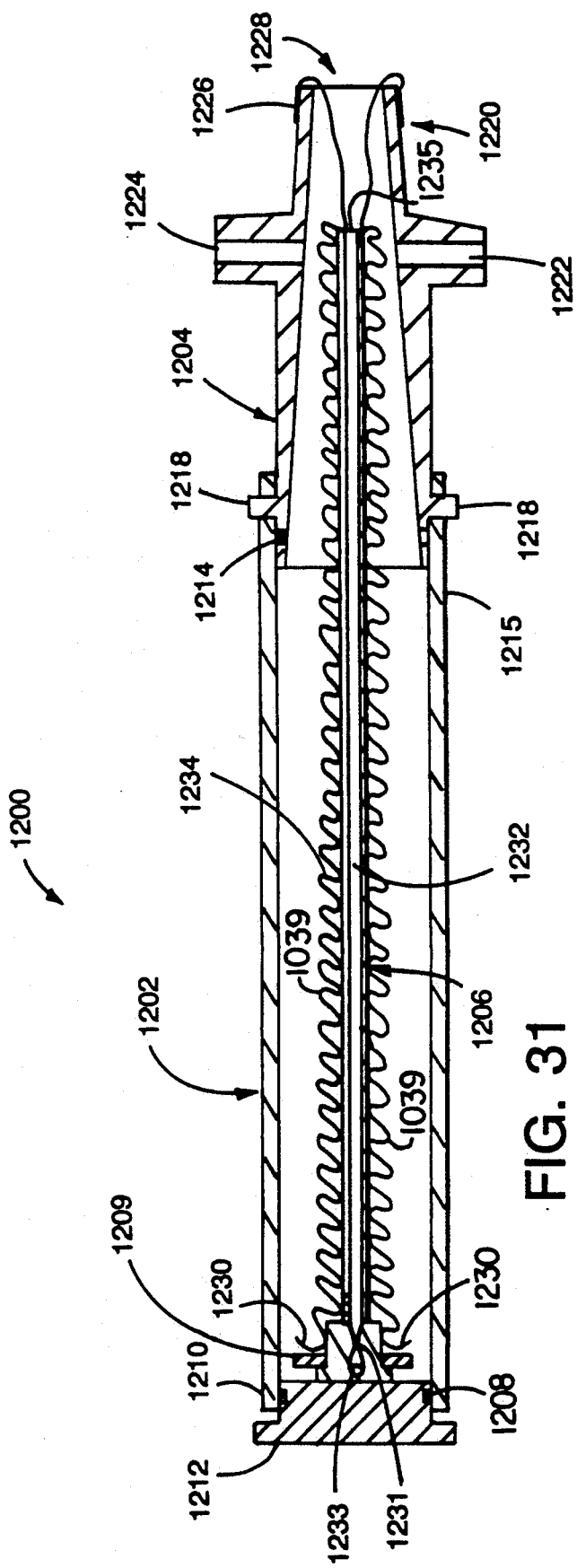
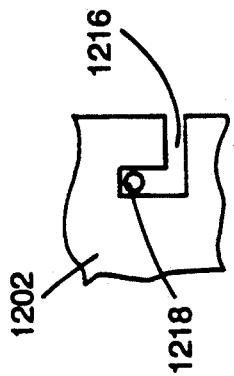
FIG. 31
FIG. 31A

FACILITATING ENDOSCOPY

This is a continuation of application Ser. No. 07/536,205, filed Jun. 11, 1990, now abandoned, which is a continuation is part of Ser. No. 07/284,067, filed Dec. 13, 1988, now abandoned.

BACKGROUND OF THE INVENTION

This invention relates to endoscopy and to materials suitable for use as everting liners for emplacing an instrument, such as an endoscope or a colonoscope, into the body.

Colon cancer is the most common visceral malignancy in the United States. There is substantial evidence that nearly all colonic malignancy has its origin in previously benign polyps, and that most colon cancer could be prevented if these polyps could be detected and removed while they are still benign.

A diagnostic procedure generally employed when malignancy of the large intestine is suspected is colonoscopy, in which the interior of the colon is examined by means of an elongated flexible fiber optic endoscope, known generally as a colonoscope.

A colonoscope for use in transanal colonoscopy is an instrument that typically includes a flexible tube sufficiently long that, when fully inserted into the colon through the anal canal, it can extend through the full length of the colon so that its proximal (inward) end reaches to the cecum. Colonoscopes can be nearly six feet long, and can have a diameter as little as about one-half inch. The proximal tip, that is, the portion about six inches long at the proximal end, is typically maneuverable by manipulation of controls at the other (distal) end. Incorporated in the tip are a light source and fiber optics for illumination and visual observation; and tools for carrying out irrigation, suction, and surgical procedures such as polyp removal.

The procedure most commonly followed for a colonoscopic examination is first to insert the colonoscope by way of the anal canal in a proximal direction into the colon as far as desired, making only a cursory inspection along the way, and then to withdraw the colonoscope distally, while examining the colon more thoroughly, performing biopsies, or removing polyps as appropriate. For an examination of the entire colon, the colonoscope is inserted through the anal opening and the anal canal into the rectum, then advanced through the sigmoid flexure into the descending colon, then from the descending colon through the left colic flexure (the splenic flexure) into the transverse colon, and then from the transverse colon through the right colic flexure (the hepatic flexure) into the ascending colon as far as the caecum. Insertion is effected by maneuvering the colonoscope tip so that it is aimed in the proper direction while (at the distal end) grasping the colonoscope at a point outside the body near the anal opening and pushing inward. The colonoscope is sufficiently stiff that it can be inserted without buckling even when many pounds of pushing force are applied.

Advancing the colonoscope tip within the colon is a difficult procedure, and it can be particularly difficult to advance the instrument through the sharp bends of the colon at the sigmoid flexure and the splenic flexure. As the instrument is worked through these bends the sigmoid colon distends and the pressure of the colonoscope on the colon walls tends to stretch that portion of the colon through which the instrument has already passed rather than advancing the tip further into the colon. In some instances, and particularly when the colon has been irritated or sensitized by the movements of the colonoscope within it, reflex action by the colon wall musculature can cause the colon to constrict around the colonoscope during insertion through these bends, aggravating the tendency of the colon to distend lengthwise. Muscle relaxants used to relax the circumferential colonic musculature can prevent this reflex constriction, but such relaxants can also relax the longitudinal colonic musculature, resulting in still further lengthwise stretching of the colon rather than proximal advancement of the colonoscope tip.

Insertion of the instrument can be uncomfortable for the patient, and the physician inserting the colonoscope may rely to some extent on the patient's complaints as an indication that the instrument has been misdirected. In cases where the procedure is acutely painful, anaesthetics can be used, but they also deprive the physician of the benefit of patient response, and moreover can require postanaesthetic recovery procedures.

Moreover, there is a substantial risk of perforation of the colon by the tip of the colonoscope during insertion, even when performed by surgeons having some experience with the procedure. Although some surgeons have been able, through care and skill, virtually to eliminate the risk of perforation, there exists a finite rate of complications resulting from diagnostic colonoscopy.

Although the inspection itself of the colon, carried out during withdrawal of the instrument, typically takes only about ten minutes' time, insertion of the colonoscope typically takes as much as 50 minutes' time, owing to difficulties in inserting the instrument and because of the care that the physician must take to reduce the likelihood of harm to the patient. Too often the insertion is halted when the tip is at a point far short of the caecum, because a portion of the colon already negotiated by the colonoscope (particularly the sigmoid flexure or the splenic flexure) may constrict tightly upon the colonoscope and prevent further advance, or because the patient cannot tolerate the procedure any further or because the physician is fearful of the danger to the patient, or for some other reason. As a result, the diagnosis is incomplete because a portion of the colon proximally beyond the farthest point reached by the tip escapes examination.

It is known to aid inspection of the inner wall of the colon by everting into the colon a flexible tube which remains generally immobile with respect to the colon wall. An object such as a medical instrument can be drawn into the intestine by the everting tube as the eversion of the tube progresses.

SUMMARY OF THE INVENTION

In a general feature of the invention, at least a portion of a flexible liner is emplaced to form within the intestine a first tube within a second tube, the first tube defining a lumen lying within the intestine and having a distal end accessible via the anal opening from outside the body; and thereafter an instrument is passed into the distal end of the lumen.

Preferred embodiments include the following features. The flexible liner is emplaced by eversion. One end of the liner is folded back upon itself to form first and second tubes connected along an annular fold; the annular fold is introduced into the anal opening; and the space enclosed between the first and second tubes is pressurized at low pressures not greater than 10 pounds per square inch, preferably less than 3 pounds per square inch. The first and second tubes are collapsed against each other prior to passing the instrument into the lumen. The tubes are collapsed by reducing the pressure in the space enclosed between the first and second tubes. A proximal tip of the instrument is passed through the lumen and beyond a proximal end of the emplaced flexible liner.

Preferred embodiments include the following features. The space between the tubes may be pressurized in an oscillating manner during eversion; and successive portions of the inner liner are pulled away from a storage device on which they were gathered. The withdrawal of portions of the liner is aided by mechanically applying intermittent force to the inner liner to free it from the storage device. The varying pressure is applied in coordination with the intermittently applied mechanical force. Specifically, the pressure is decreased when the mechanical force is being applied. The liner storage device includes an internal passage and an external wall supporting the liner, and the force is mechanically applied by means of a tool passed via the storage device passage. In some embodiments, the force is mechanically applied by inflating a balloon against a wall of the liner.

In another general feature, the liner comprises a material characterized by having a wall thickness to diameter ratio and a zero strain elasticity modulus whose product is less than 4.0 lb/inch$^2$, preferably less than 1.0 lb/inch$^2$, and a wall thickness to diameter ratio and a 100% strain modulus of elasticity whose product is greater than 0.5 lb/inch$^2$, preferably greater than 2.0 lb/inch$^2$.

In preferred embodiments, the liner comprises polyurethane or latex; the liner is at least sufficiently long to reach proximally beyond the sigmoid flexure when fully everted within the large intestine, preferably at least 12 inches long; the liner is at least sufficiently long to reach beyond the splenic flexure when fully everted within the large intestine, preferably at least 30 inches long; the distal port is configured and dimensioned to receive a leading end of the instrument; and the distal port is sealed during eversion.

In another general feature of the invention, opposite ends of the liner are attached to distal and proximal ports, a portion of the liner is gathered in the space between the ports, the liner defines a lumen between the ports, and a rigid guide tube lying within the lumen and between the ports provides an unobstructed passage for the instrument.

In preferred embodiments, a portion of the liner is gathered along and supported by the outside wall of the guide tube, and the tube is straight, and colinear with both of the ports. A mechanism is located in the vicinity of one end of the guide tube for contacting the liner and aiding withdrawal of the liner from the guide tube. The mechanism may include a roller whose outer surface contacts the liner and a support for the roller, the support having a structure for permitting the roller to turn when the liner is being withdrawn from the guide tube, while resisting the turning of the roller when the liner is being moved in the opposite direction. The guide tube has an internal passage and an external wall supporting the liner, and the force is mechanically applied by means of a tool passed via the storage device lumen. In other embodiments, the force is mechanically applied by inflating a balloon against a wall of the liner.

In another general feature of the invention, a tube extends distally from the distal port, the end of the liner attached to the distal port is everted over and gathered along the tube, and the pressurizer simultaneously causes the liner to evert beginning near the end attached to the proximal port while enabling the gathered portion of the liner to slide along and be released from the tube.

In preferred embodiments, there are means for selectively depressurizing the everted liner. A walled passage is connected to the distal port for bridging the distance from the distal port to the anal sphincter of the patient.

The liner forms a pathway for advancing the colonoscope and provides for easier, safer, and less painful insertion of the instrument, reducing the need to use anaesthetics during the procedure, and reducing the tendency for stretching, spearing, and distension of the colon during insertion. The invention can substantially reduce the time required for insertion of the instrument, reducing the cost of the procedure and increasing its availability as a diagnostic and preventive measure. The flexible tube can be everted using low fluid pressures, providing safe and gentle lumen-following emplacement of the liner. Once the liner is emplaced, the colonoscope can be slid within the liner lumen, contacting only the inner wall of the liner, so that over the length of the liner it does not contact the colon wall. The inner and outer tubes of the liner may slide freely over one another, during both emplacement of the liner and insertion of the colonoscope, further isolating the movement of the advancing instrument from the colon wall.

Another general aspect of the invention is directly bonding a layer of lubricous material to a surface of a layer of elastomeric material.

Preferred embodiments include the following features. The lubricous material is polyvinylpyrrolidone (PVP), and the elastomeric material is polyurethane. The PVP is bonded to the polyurethane surfaces by applying heat and pressure (together or in separate steps) between the layers of PVP and polyurethane. Preferably, this is done by passing the polyurethane layer and a release paper which supports the PVP between rollers that are heated (e.g., at between 290 degrees and 320 degrees Fahrenheit). The PVP is transferred from the release paper and securely laminated to the polyurethane surfaces. Optionally, and to improve the durability of the PVP-polyurethane bond, the laminated layers are "baked" (e.g. at 290° F. to 320° F. for about two hours). This likely cross links the PVP to some extent, which improves its resistance to washing off. Gamma radiation is applied as an additional or alternative way of forming the cross links.

The PVP is directly bonded to opposite planar surfaces of a polyurethane sheet. The PVP coating is applied in the form of one or more parallel stripes on one surface of the polyurethane sheet and as a continuous sheet on the other surface. At least one tube having PVP-coated interior and exterior surfaces is formed from the sheet. In one embodiment, this is done by folding the sheet along an axis so that uncoated portions of polyurethane that bound the PVP stripe are aligned; the uncoated portions are then secured together along a seal that is parallel to the axis, and the sheet is cut along this seal to separate the tube. In another embodiment, the tube is formed by placing two such PVP coated sheets face-to-face and securing them together along seals defined by uncoated portions of polyurethane that bound the PVP stripes. If the PVP is sufficiently thin, the seals may be made through the PVP.

In another aspect of the invention, the PVP-coated tube forms a liner which is emplaced into a body cavity (such as the colon). Because the lubricous PVP is disposed on the exterior and interior surfaces of the liner, the liner is extremely slippery, particularly when exposed to water. This facilitates both the emplacement of the liner and the subsequent passage of an instrument (such as a colonoscope) into the colon via the liner. Because adhesive material is not used or needed to secure the PVP to the polyurethane, the liner includes no foreign substances that may irritate or harm the colon. The bond is durable, and the PVP does not wash off during storage or when the liner is immersed in water during use.

The liner is emplaced by eversion to form within the colon an inner tube within an outer tube. The inner tube defines a lumen within the body cavity and is accessible from outside of the body to allow the insertion of an instrument, such as the colonoscope. The polyurethane and PVP may have a wide range of thicknesses, but should be sufficiently thin to allow the liner to be readily everted by the application of a small amount of water pressure (two psi or less). For example, the polyurethane is on the order of 5 mils thick, and each PVP coating is between 0.08 mils and 0.5 mils in thickness. Preferably, the liner is everted and emplaced solely by applying water pressure without mechanical assistance, thereby rendering the procedure less uncomfortable for the patient, and less potentially dangerous as well.

The ease with which the liner can be everted is enhanced by the absence of adhesive material between the polyurethane and the PVP. One reason for this is that the total thickness of the liner is minimized. In addition, adhesive materials are generally less pliable than either the polyurethane or the PVP.

Another aspect of the invention is apparatus for emplacing a flexible liner into a body cavity that includes a housing for storing the liner and a guide member within the housing about which the liner is at least partially gathered; the housing receives fluid (such as water) during emplacement to cause the liner to be withdrawn from the guide member and advanced out of the housing and into the body cavity by eversion; the guide member also receives fluid and applies the fluid between an exterior surface of the member and the liner to assist in removing the liner.

Preferred embodiments include the following features. The guide member is a hollow tube that includes a slot for channelling the fluid from the interior of the tube to its exterior surface. The tube is tapered to a reduced diameter in the direction of emplacement to simplify its manufacture (e.g., by injection molding).

In yet another aspect of the invention, the liner emplacement apparatus includes a housing for storing the liner and which is removably mounted to inserter to which one end of the liner is attached; an inlet receives fluid to cause the liner to be withdrawn from the housing and advanced by eversion into the body via the inserter. Because the housing (which is relatively long with respect to the length of the inserter) can be removed, an instrument (such as a colonoscope) can be inserted directly through the inserter into the body cavity through the liner, thereby reducing the length of the instrument which remains outside of the body.

Preferred embodiments include the following features. The housing includes a member, such as the aforementioned slotted guide tube, about which the liner is gathered. A second end of the liner is loose within the housing so that it can be withdrawn from the housing and advanced into the body cavity (e.g., the colon) after the liner has been advanced into the body by a predetermined amount. The liner is long enough to allow it to reach the cecum.

The inlet is preferably in the inserter. After the housing is removed, a fitting is attached to the inserter in place of the housing to receive the instrument, the fitting being substantially fluid-tight so that as the instrument is inserted fluid that is added through the inlet to lubricate the liner (which is preferably the PVP-coated polyurethane described above) is inhibited from escaping from the inserter. The fitting includes a length of liner, one end of which is attached to the fitting, and the other end of which is adapted (such as with a band of elastic material wound around the end) to fit snuggly around the instrument as the instrument passes therethrough.

The superior lubricity of the liner permits easier, safer, and less painful insertion of the instrument into and through the colon, reducing the need for anesthetics during the procedure and the tendency of the colon to stretch and distend during insertion. The time needed for the colonoscopy is reduced, thereby lowering the cost of the procedure and increasing its availability and effectiveness as a diagnostic and preventive technique.

Other advantages and features will become apparent from the following description of the preferred embodiments, and from the claims.

DESCRIPTION OF THE PREFERRED EMBODIMENTS DRAWINGS

FIGS. 25 and 26 are side views (FIG. 25 is partially cut away) and FIG. 27 is a side sectional view of yet another liner emplacement device.

FIG. 27A is an enlarged, planar view of a region of the liner emplacement device of FIG. 27.

FIG. 31 is a cross-sectional view of yet another liner emplacement device, and FIG. 31A is an enlarged, planar view of a region of the device.

STRUCTURE AND USE

Liner Emplacement Device and Everting Liner

Figure 1:
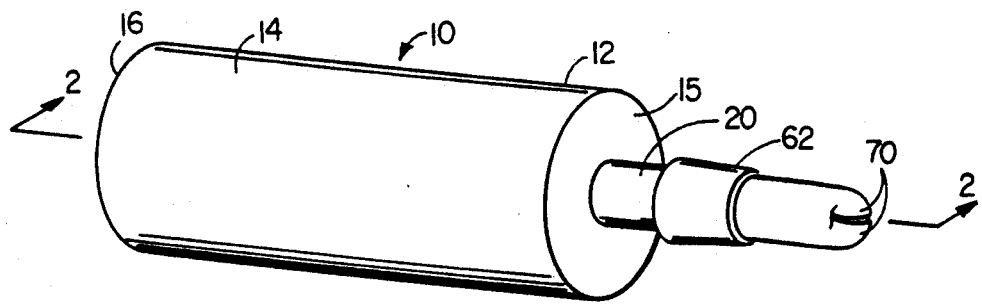
FIG. 1 is a perspective view of liner emplacement apparatus.
Figure 2:
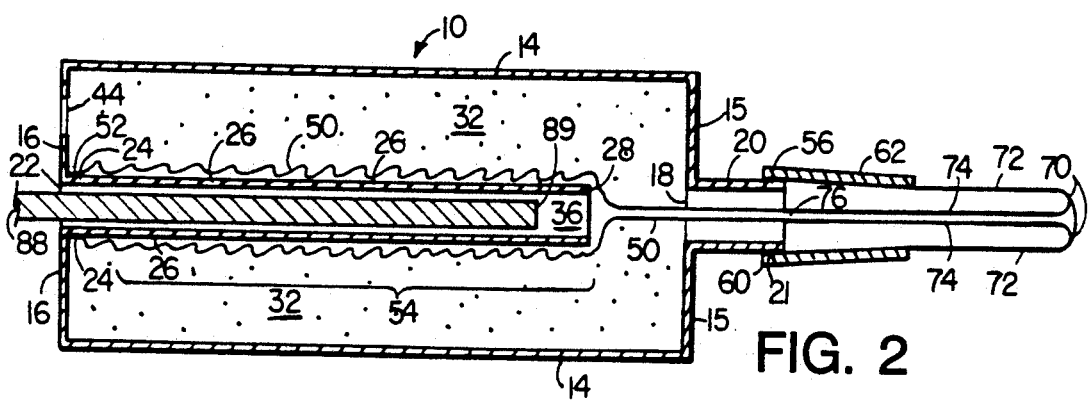
FIGS. 2 and 3 are sectional views at 2—2 of FIG. 1 showing two stages of eversion of the flexible tube.
Figure 3:
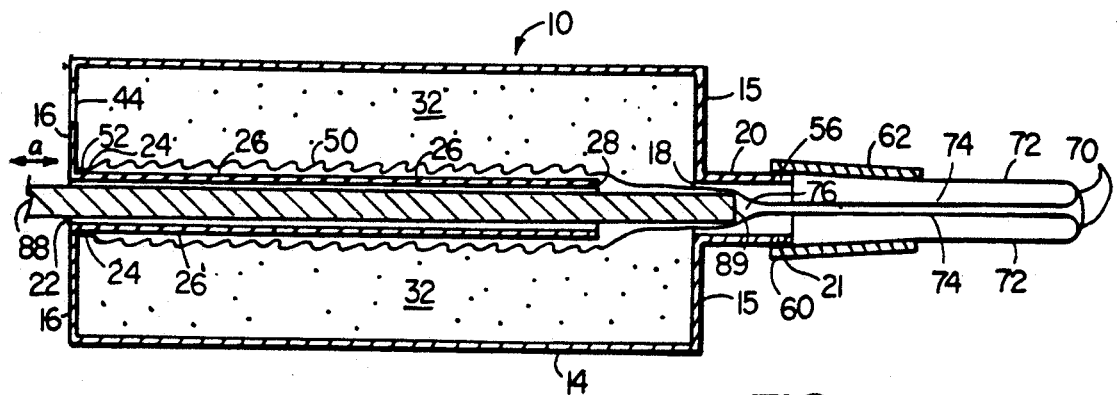
Figure 5:
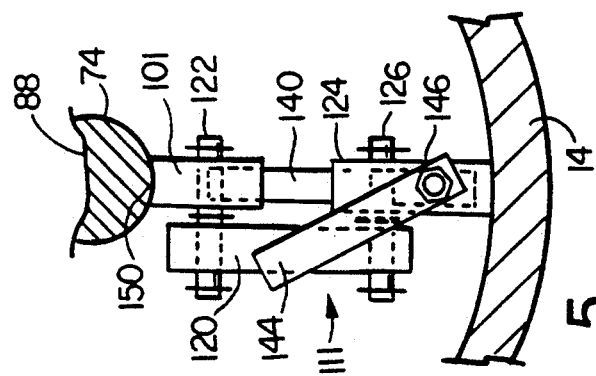
FIG. 5 is a front view of a representative roller and its support with the colonoscope and outer wall shown in section.

Referring to FIGS. 1, 2 and 3, a liner emplacement device 10 includes a sterilized, disposable container 12 defined by a cylindrical wall 14 and capped by front and rear walls 15, 16. A port 18 in front wall 15 opens into an external nozzle 20, and a port 22 in rear wall 16 is surrounded by an internal flange 24. A rigid guide tube 26 is affixed to and extends from rear flange 24 forward toward front port 18, and is oriented so that rear port 22, rigid guide tube 26, and front port 18 are generally in axial alignment. Container 10 encloses chamber 32, into which fluid can be pumped from a reservoir (not shown) outside container 10 by way of a fluid port 44 in rear wall 16.

A thin-walled flexible elastomeric tube about ⅜ inch in diameter (which when everted will serve as the colon liner), and about 80 inches long for colonoscopy in an adult human (and, for example, about 36 inches long for sigmoidoscopy), is made ready for emplacement in the colon generally as follows. One end 52 of flexible tube 50 is mounted over rear flange 24. Initially the major portion 54 (FIG. 2) of tube 50 is stored within chamber 32 by gathering the major portion 54 of tube 50 over guide tube 26. The other end 56 of tube 50 is passed through front port 18 and nozzle 20, and is turned inside out and mounted tightly over free end 21 of nozzle 20. An end 60 of an introducer tube 62 is slipped over tube end 56 so that tube end 56 is tightly held between end 60 of introducer tube 62 and end 21 of nozzle 20. Introducer tube 62 is made of a material, such as for example a polymer, that is sufficiently stiff that it can be inserted transanally beyond the rectal sphincter, yet sufficiently pliable that it does not cause damage to the tissues of the anus or rectum, or undue discomfort to the patient. Introducer tube 62 bridges the distance from the tube end 56 to the anal sphincter of the patient.

Now, introducer tube 62 is inserted into the anal canal (not shown) of a patient, and eversion of flexible tubing 50 into the colon is effected as follows. Container 10 is filled with fluid by introducing the fluid into chamber 32 by way of rear fluid input port 44. As the fluid fills chamber 32, tube 50 swells outward, exits nozzle 20, passes through introducer tube 62, and begins to evert at an annular everting margin 70. As tubing 50 everts, margin 70 advances in a forward direction proximally within the colon, in the process forming an outer liner tube 72 and continually drawing, as a trailing tube portion 74, the stored portion 54 of tube 50 from guide tube 26 and out of chamber 32 through front port 18, nozzle 20, introducer tube 62, and outer liner tube 70. By the nature of the eversion process, there is little or no sliding between the outer liner tube 72 and the inner wall of the colon. As trailing tube portion 74 is withdrawn from guide tube 26, that portion of the tube in front of end 28 of guide tube 26 is compressed upon itself by the pressure of the fluid between the trailing tube portion and the outer, already everted outer liner tube 72, while the stored portion 54 of tube 50 is pressed against storage support 26, and is thereby prevented from collapsing upon itself.

Figure 17:
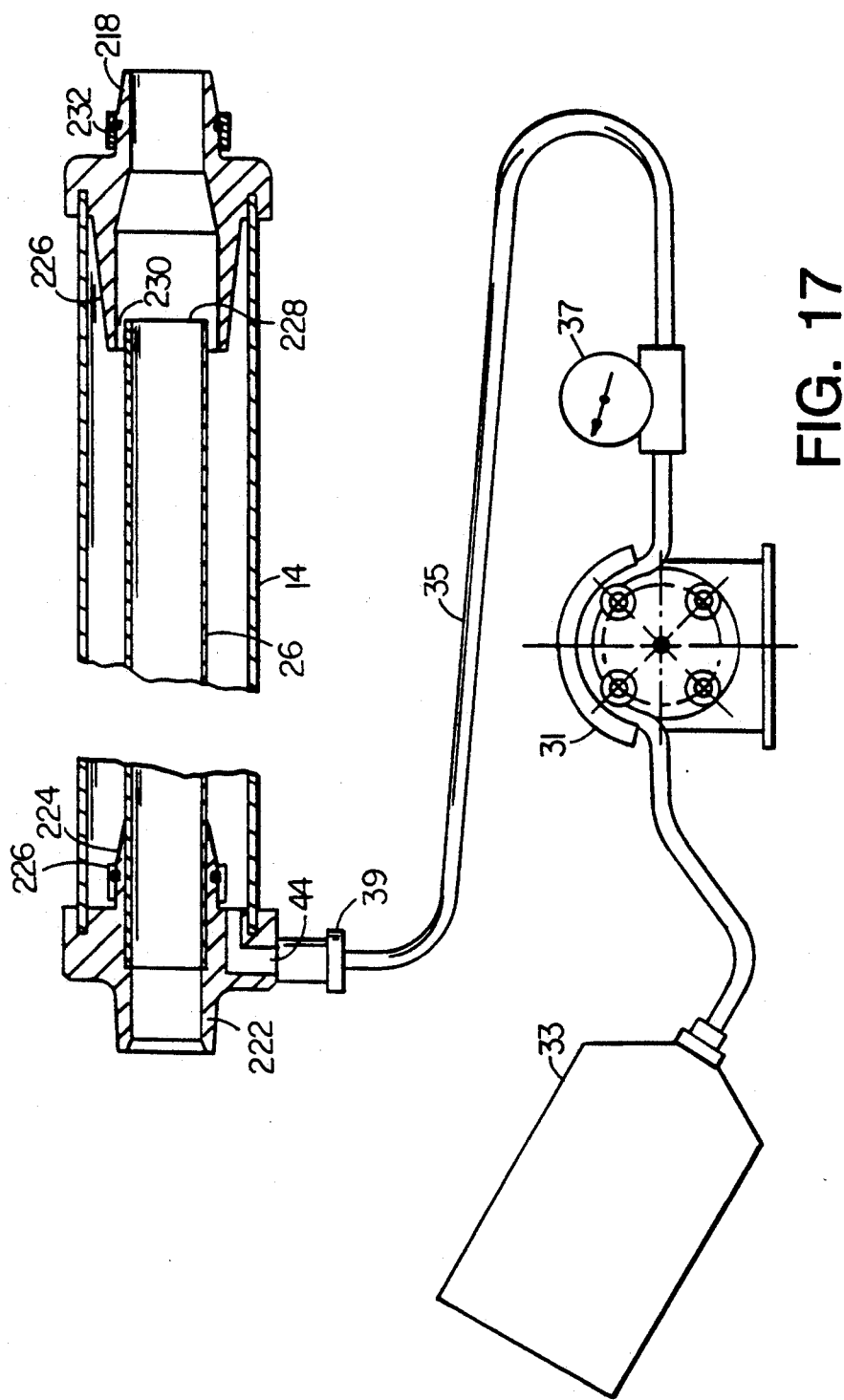
FIG. 17 is a sectional view, partially broken away, of an alternative emplacement device.

Referring to FIG. 17, in a preferred embodiment, guide tube 26 (12.5 inches long by 0.688 inches diameter) is supported at one end on a rear port molding 222. Molding 222 has a leading tapered end 224 which tapers to meet the outer wall of guide tube 26. A clamping sleeve 226 is press fit over tapered end 224 to hold one end of the liner (not shown) in place. At the other end of outer wall 14 (13.25 inches long, 1.5 inches diameter), external nozzle molding 220 has a trailing cylindrical portion 226 which extends back beyond the proximal end 228 of guide tube 26 leaving a cylindrical passage 230 through which the liner can pass freely during eversion. Passage 230 is small enough to prevent the passage of kinks or folds in the liner, which could interfere with liner eversion. The inner wall of portion 226 is 0.875 inches in diameter. A second clamping sleeve 232 holds the other end of the liner on the nozzle 220.

As shown in FIG. 17, peristaltic pump 31 pumps fluid into chamber 32 from reservoir 33 by way of flexible tubing 35 and coupler 39 through fluid port 44. A pressure gauge 37 is situated between pump 31 and fluid port 44 for monitoring the eversion pressure.

The pressure of the everting fluid within the chamber pressing the stored liner against the guide tube can result in a frictional resistance to withdrawing the trailing portion of the tube from the guide tube. As the pressure is increased, any such resistance also increases. As an aid in withdrawing stored tube 54 from guide tube 26, colonoscope 88 is inserted through rear port 22 into space 36 within guide tube 26 and moved frontward, so that its proximal end 89 passes into the lumen 76 of trailing portion 74 of tube 50 and contacts the collapsed tubing wall. Although generally the lumenal surface of the liner has a low frictional coefficient with respect to the colonoscope surface, so that the colonoscope slides easily within the emplaced liner, the fluid pressure presses the collapsed tubing wall against the colonoscope tip, providing some degree of traction between the colonoscope tip and the collapsed tubing wall. As a result, the frontward-moving colonoscope tip can carry this collapsed tubing wall frontward, withdrawing a further trailing portion of the tube from end 28 of guide tube 26. Then colonoscope 88 is moved rearward until its end 89 is withdrawn from trailing portion 74 of tube 50 back to space 36 within guide tube 26. In this fashion, the colonoscope is reciprocally moved back-and-forth, as indicated by arrows a (FIG. 3), between one position, e.g., FIG. 2, and a second position, e.g., FIG. 3, aiding with each frontward stroke in withdrawing a further portion of tube 50 from guide tube 26.

Moreover, the fluid pressure within chamber 32 can be varied (by a pressure regulator, not shown) to provide pulses of greater pressure alternating with intervals of less pressure, and the pulsations of pressure cooperate with the reciprocal movement of the colonoscope to further assist the colonoscope tip in drawing the stored tube off from the guide tube. As the colonoscope is moved rearward, a pulse of greater pressure is provided, promoting eversion of the tubing and advancement of the everting margin. Then, as the colonoscope is moved frontward, an interval of less pressure is provided, reducing the frictional resistance between the guide tube and the stored tube, and allowing the stored tube to be more easily drawn frontward by the colonoscope.

Figure 4:
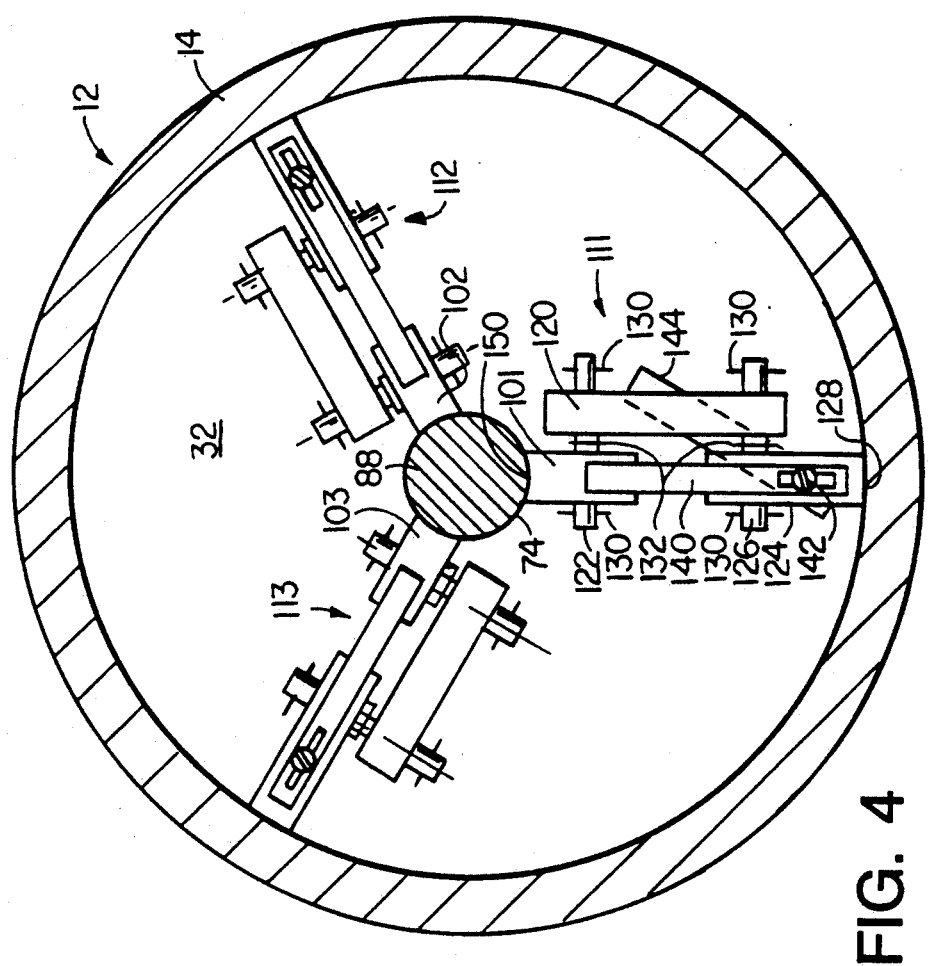
FIG. 4 is a rear view of a roller structure for aiding delivery of the everting tube from the guide tube with the colonoscope and outer wall shown in section.

Referring to FIGS. 4 through 7, to aid eversion rollers can be provided to press the trailing portion of the tube against the moving colonoscope tip to increase the traction between the colonoscope tip and the collapsed tubing wall of the trailing portion of the tube. As shown in FIG. 4, rollers 101, 102, 103 are in tangential contact with trailing portion 74 of tube 50, so that when colonoscope 88 is passed into tube lumen 76 (FIG. 3), trailing portion 74 of tube 50, is pressed by rollers 101, 102, 103 onto the surface of colonoscope 88. Rollers 101, 102, 103 are supported by roller supports 111, 112, 113, affixed in evenly spaced radial arrangement to cylindrical wall 14 of container 12. Roller supports 111, 112, and 113 are essentially identical. Roller 101 is rotatably attached by means of shaft 122 to pivoting member 120. Pivoting member 120 is pivotally attached by means of shaft 126 to fixed member 124, which is affixed at 128 to wall 14 of container 12. The axes of shafts 122, 126 are generally normal to a plane passing through 128 and through the long axis of container 12. O-rings 132 located midway along shafts 122, 126 serve as spacers to inhibit contact between pivoting member 120 and roller 101 and fixed member 124; and retainer pins 130 keep roller 101 and members 120, 124 in place on shafts 122, 126. Roller stop 140 and pivot stop 144 are affixed to fixed member 124 by means of bolt 142 and nut 146.

Figure 6:
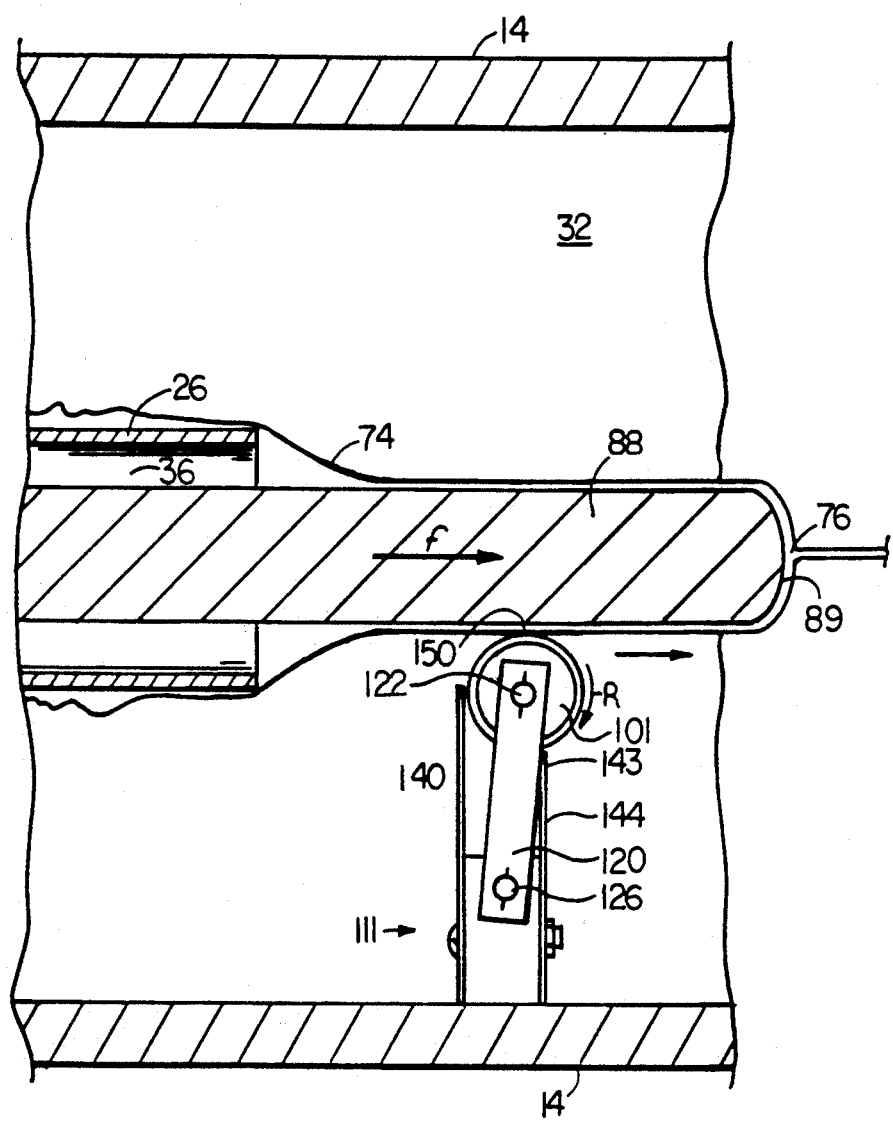
FIGS. 6 and 7 are side sectional views showing two positions of a representative roller and its support.
Figure 7:
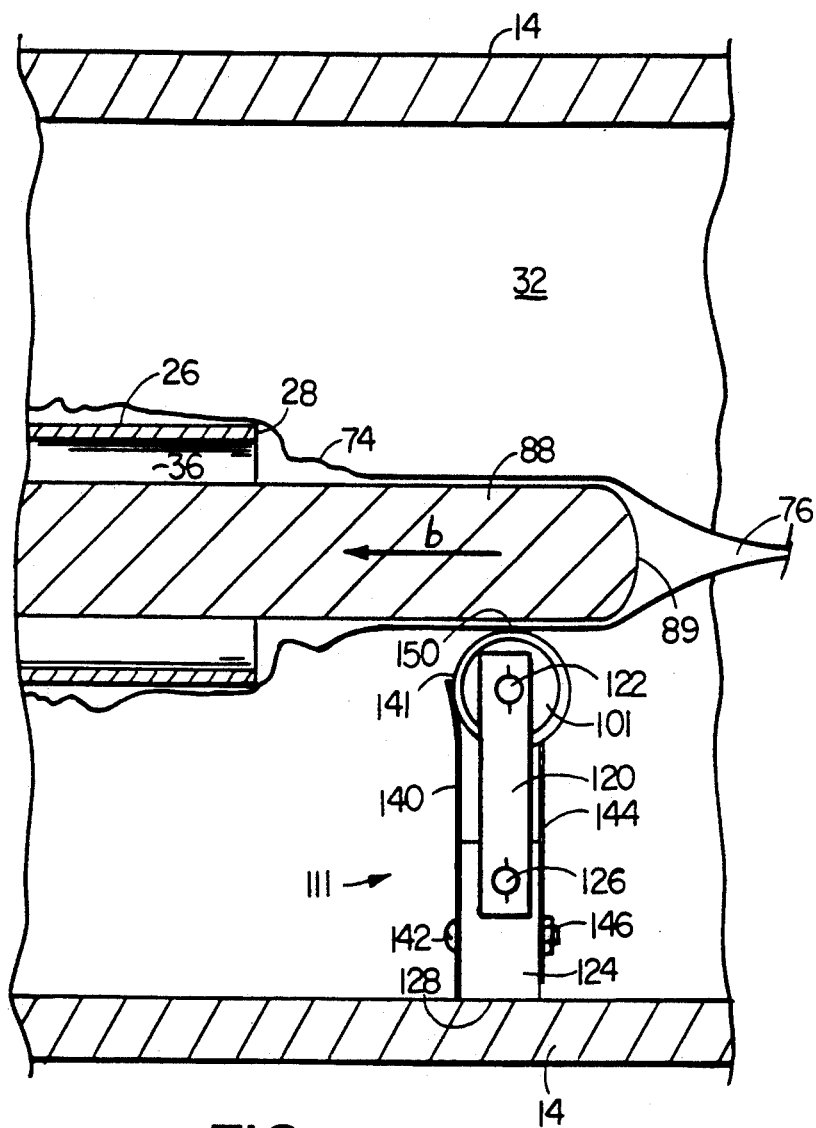

FIGS. 6 and 7 show the cooperation of roller 101 and roller support 111 with trailing portion 74 of tube 50 and colonoscope 88 when the colonoscope is moved reciprocally back-and-forth t assist in withdrawing the stored tube from the guide tube. As colonoscope 88 is moved frontward, as indicated by arrow f in FIG. 6, roller 101 presses trailing portion 74 of tube 50 against colonoscope 88 at the point 150 of tangential contact, increasing the friction between the tube wall and the colonoscope, aiding in withdrawing stored tubing 54 off from guide tube 26. As stored tubing 54 is drawn frontward, it causes pivoting member 120 to pivot frontward and it causes roller 101 to rotate as shown by arrow R. As pivoting member 120 pivots frontward, it contacts pivot stop 143, as shown in FIG. 6, whereby further frontward pivoting of member 120 is inhibited. Then, as colonoscope 88 is withdrawn backward, as indicated by arrow b in FIG. 7, the tubing wall is carried backward, owing to traction between it and the colonoscope. This backward movement of the tubing wall causes pivoting member 120 to pivot backward until roller 101 contacts roller stop 140 as shown in FIG. 7, whereby further backward pivoting of member 120 and rotation of roller 101 are inhibited. The cylindrical contact surface of roller 101 is of a material having a high frictional coefficient with respect to tube 50. As a result, as the colonoscope is further withdrawn, tube 74 is inhibited by contact with stopped roller 101 from further movement backward, and as the traction between the colonoscope and the tube is thereby overcome, the colonoscope slides rearward out from the trailing portion of the advancing tube. Further reciprocations of the colonoscope into the lumen of the collapsed trailing portion of the tube follow, withdrawing further stored tubing from the guide tube, until the tubing has been everted to the desired extent.

When eversion of tube 50 has proceeded to the desired point, the source of fluid to rear port 44 is removed, or the pressure in chamber 32 is allowed to drop, so that the fluid is allowed to drain out from container 10 through rear port 44. This relieves the pressure that had compressed the trailing portion of the everting tube to collapse upon itself during eversion, and permits inner liner tube 74 of everted tube 50 to collapse upon outer liner tube 72 of everted tube 50. Then the colonoscope 88 can be introduced through rear port 22, through the space 36 within guide tube 26, and through the lumen 76 formed by the inner surface of inner liner tube 74 of fully everted tube 50, sliding along the lumen 76 of the fully everted liner. Thus, less than the full length of the liner can be emplaced if desired, leaving the tube in part on the guide tube, and permitting insertion of the colonoscope through the still-stored portion by way of rear port 22 and the enclosed space 36 within storage support 32.

Figure 8:
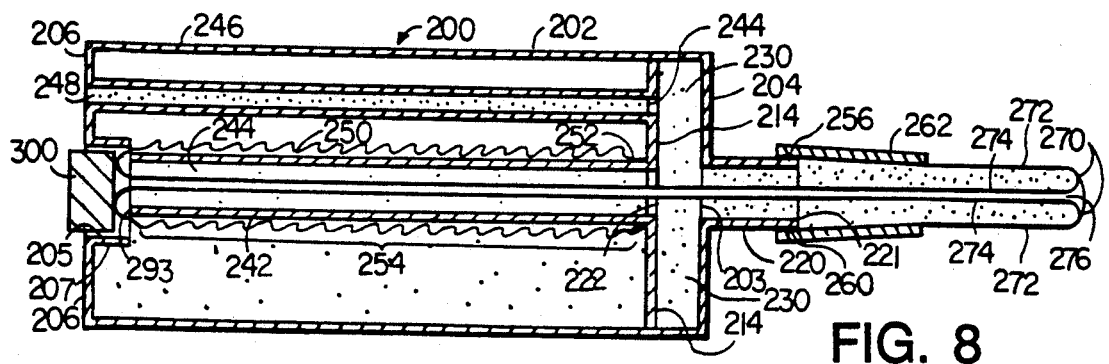
FIGS. 8 and 9 are sectional views of alternative liner emplacement devices.
Figure 9:
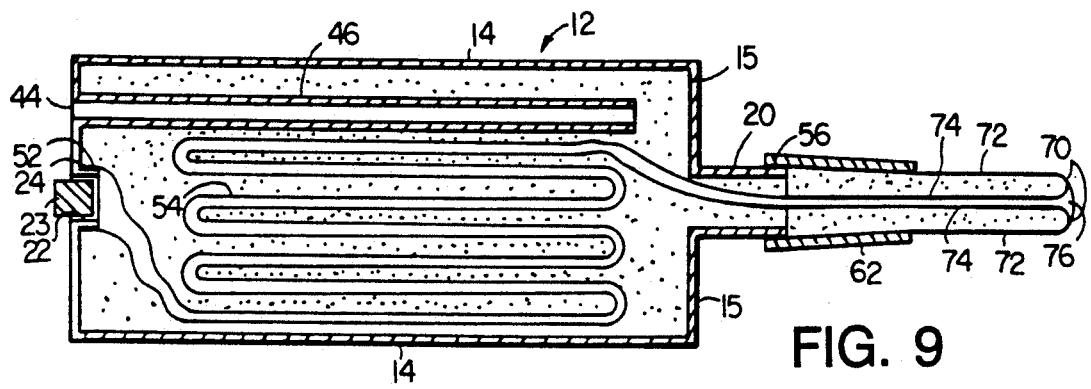
Figure 10:
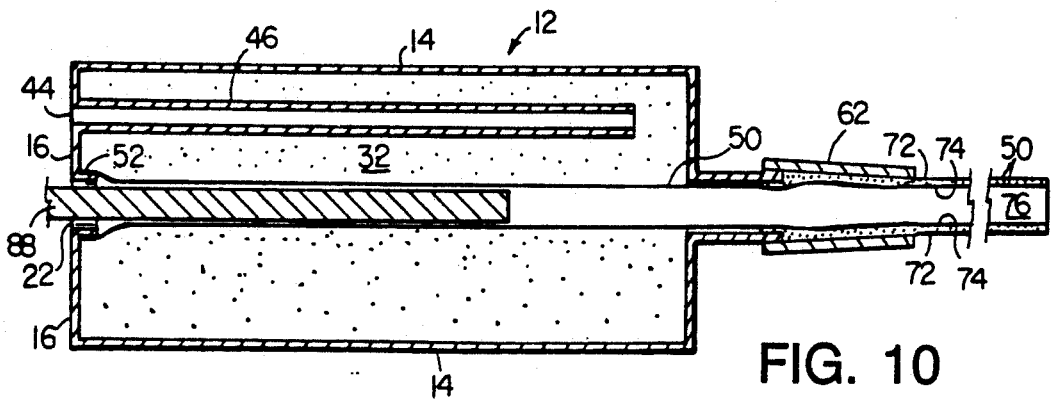
FIG. 10 is a sectional view, like FIG. 9, with the flexible tube fully everted.

Referring to FIGS. 9 and 10, alternatively the guide tube may be eliminated, and the tubing may be stored by coiling or stacking it loosely in the chamber. Apart from the lack of a guide tube the tubing is made ready for emplacement generally as described above with reference to FIG. 2. The embodiment of FIGS. 9 and 10 has the advantage of being structurally simpler than the embodiments shown in FIGS. 2 through 8; but it has the disadvantage, as will be apparent from the description below with reference to FIG. 10, that the full extent of the tubing must be everted before the colonoscope can be inserted through it, because the colonoscope cannot pass through the folds and turns of the coiled or stacked stored tubing.

In use, introducer tubing 62 of FIGS. 9, 10 is inserted into the anal canal of the patient, and flexible tube 50 is everted into the colon as follows. A plug 23 is fitted into rear port 22, and chamber 32 is filled with fluid via port 44 and conduit 46. As the fluid fills chamber 32, flexible tube 50 collapses, as shown in FIG. 9. As the fluid pressure is increased, tube 50 begins to evert at an annular everting margin 70. As tubing 50 everts, margin 70 advances into the colon, and in the process forms an outer liner tube 72 and continually draws a trailing tube portion 74 from storage chamber 32 in effect providing a double walled liner within the colon. By the nature of the eversion process, there is little or no sliding between the outer liner tube 72 and the inner wall of the colon.

Referring to FIG. 10, when tube 50 is completely everted, the source of fluid is disconnected from rear input port 44 and the fluid allowed to drain from container 12. This permits trailing tube portion 74, which now constitutes an inner liner tube, to collapse upon outer liner tube 72 of everted tube 50. Then plug 23 is removed from rear port 22, and the colonoscope 88 is introduced, as shown generally by arrow i, through rear port 22 and through the lumen 76 formed by the inner surface of inner liner tube 74 of fully everted tube 50, sliding along the lumenal surface of the fully everted liner.

The flexible tube forming the liner preferably is thin and is of an elastomeric material having a low initial modulus of elasticity; that is, initially the wall is easily stretched so that only low fluid pressures are required for eversion. Preferably, the product of the tube wall thickness to diameter ratio and the initial (that is, at zero strain) modulus of elasticity is less than 4 pounds per square inch, and more preferably less than 1 pound per square inch. The tube preferably has limited distensibility, so that it does not "balloon", which would cause distension and stretching of the colon during eversion. The tube preferably is of a tough material, so that it resists spearing and penetration by the colonoscope during insertion of the instrument. Preferably, the product of the liner wall thickness to diameter ratio and the 100% strain modulus of elasticity is greater than 0.5 pound per square inch and more preferably greater than 2 pounds per square inch. The walls of the tube preferably have a low coefficient of friction, both with respect to one another, so that they move easily against one another during eversion, and with respect to the colonoscope, so that the colonoscope does not bind as it slides through the lumen of the liner.

Polyurethane is a preferred tube material, as it has low distensibility (that is, stress rises rapidly and non-linearly with strain), and is tough and penetration-resistant. For colonoscopy, preferably a polyurethane liner has a diameter between about ½ inch and 1 inch, and a wall thickness between about 0.002 inch and 0.007 inch. Polyurethane tube about ¾ inch in diameter and having a wall thickness 0.003 inch formed by dielectric sealing of 3 mil polyurethane sheet can be everted using fluid pressures of a few pounds per square inch, when lubricated as described further below.

Latex rubber is also a suitable tube material for low pressure eversion. Preferably a latex liner has an inner diameter between about ½ inch and about 1 inch, and a wall thickness between about 0.010 inch and 0.030 inch. Latex tube about ¾ inch in diameter and having a wall thickness 0.015 inch can be everted using fluid pressures in the range 1-2 pounds per square inch when well-lubricated. Latex is less preferred than polyurethane, however, as latex is more easily stretched and distended than polyurethane.

As noted above, the fluid pressure for effecting eversion causes the stored portion of the tubing to collapse upon itself. Without lubrication, the collapsed tubing walls stick to one another with a force that increases with increasing pressure, so that it is necessary to use tube materials having a low coefficient of friction, or to provide a lubricant that is sufficiently viscous that it is not substantially displaced from the contacting wall surfaces under the pressure of the fluid.

Moreover, the everting fluid itself must have some degree of lubricity to aid in minimizing the friction between the collapsed, not yet everted, inner portion of the tube and the everted outer portion of the tube as the inner portion slides against the outer portion during eversion. The viscosity of the everting fluid must be low enough to minimize the pressure drop between the chamber and the everting margin.

For latex liner materials, a preferred lubricant for the everting fluid is an aqueous hydrogel such as, for example, K-Y Jelly mixed with water in a proportion as great as about 30% jelly, and preferably between about 1:10 and 1:5. A preferred lubricant for the contacting surface of the collapsed tubing is an aqueous hydrogel such as, for example, K-Y Jelly and water in a proportion at least about 1:2.

An aqueous hydrogel can be suitable for a lubricating everting fluid for a polyurethane liner as well, as described generally in, for example, D.R. Shook et al., 1986, Trans. ASME, Vol. 108, pp. 168-74. More preferably the coefficient of friction of polyurethane tube and/or of the guide/storage tube is reduced by coating the wall surfaces with a hydromer such as, for example, polyvinylpyrrolidone ("PVP"), which has a very low coefficient of friction when wet, as described generally in, for example, D.R. Shook et al., 1986, Trans. ASME, Vol. 108, pp. 168-74.

Figure 11:
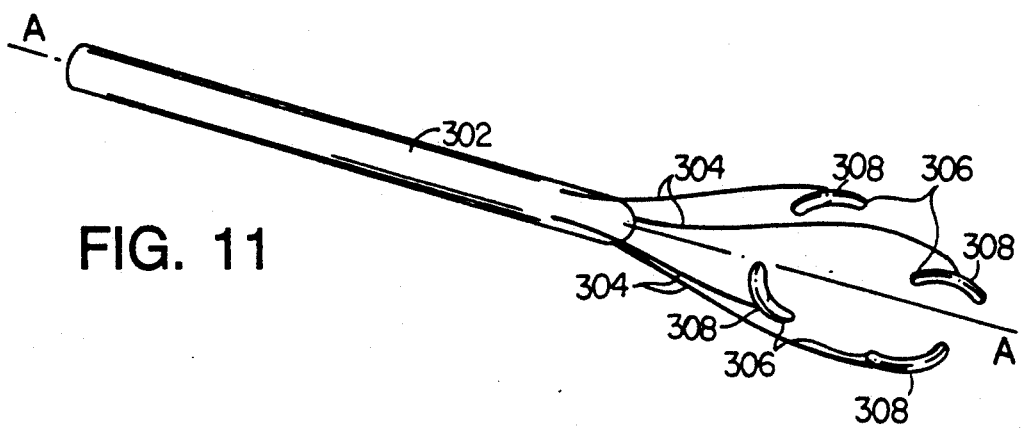
FIG. 11 is a perspective view of a liner deployment tool.
Figure 12:
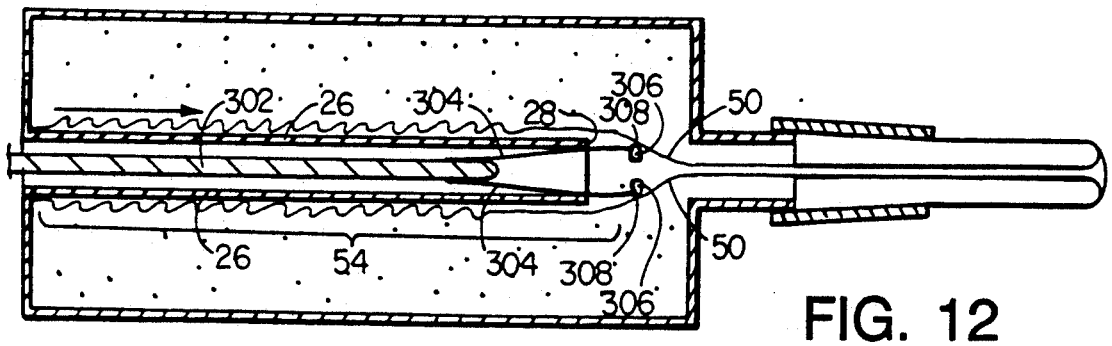
FIGS. 12 and 13 are sectional views of the liner deployment tool in two stages of use.
Figure 13:
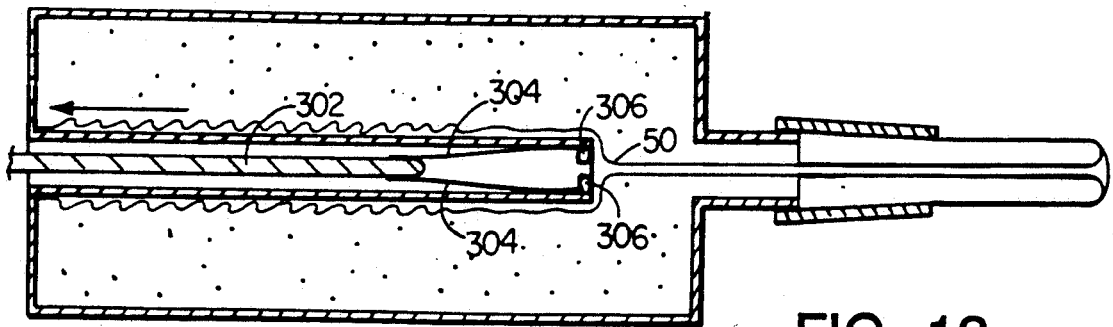

Means other than the colonoscope can be passed through rear port 22 into space 36 within guide tube 26 and reciprocated back-and-forth to aid in withdrawing stored tube 54 from guide tube 26. For example, any device configured like the colonoscope tip can be used substantially as described above. Referring to FIGS. 11 through 13, each of four feet 306 is attached to one end of a curved leg 304, and the other end of each leg is affixed to an end of a handle 302. Legs 304 are constructed of a resilient material, and are affixed to handle 302 so that the legs mutually diverge and so that when the legs or the feet are forced toward the axis the resilience of the legs tends to urge the feet divergently apart.

Referring to FIGS. 12 and 13, the legs 304 can be gathered toward the axis A—A of the handle 302, inserted feet foremost into the rear port 22 of the container, and pushed frontward within the guide tube 26. The resilience of the legs presses the feet divergently outward, so that the feet slide against the lumenal surface of the guide tube as the handle is pushed frontward until the feet 306 reach beyond the front end 28 of the guide tube 26. Then the resilience of the legs forces the feet against the liner tube. A radially outward surface 308 of each foot is provided with a material that has a high coefficient of friction with respect to the tube wall. As the handle is pushed further forward, the liner tube is carried forward by the feet, and it is drawn off from the guide tube. Then, as the handle is withdrawn rearward (FIG. 13), the legs engage first the end 28 and then the lumenal surface of the guide tube 26, which compresses the legs toward the handle axis, causing the feet to lose contact with the liner tube. The handle 302 is reciprocated in this manner frontward and rearward as fluid is introduced under pressure into the container as described above, and the reciprocating action helps to withdraw the tube from the guide tube as the liner is everted.

Figure 14:
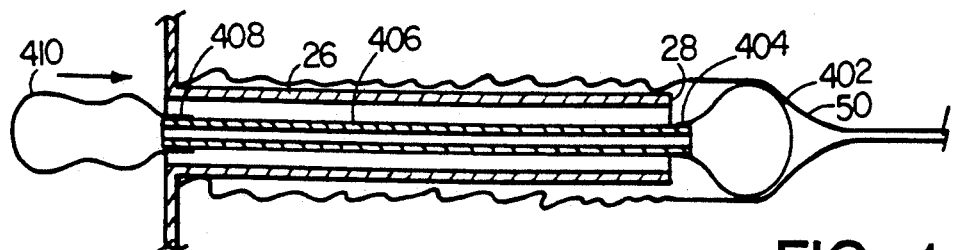
FIGS. 14 and 15 are sectional views of an alternative liner deployment aid in two stages of use.
Figure 15:
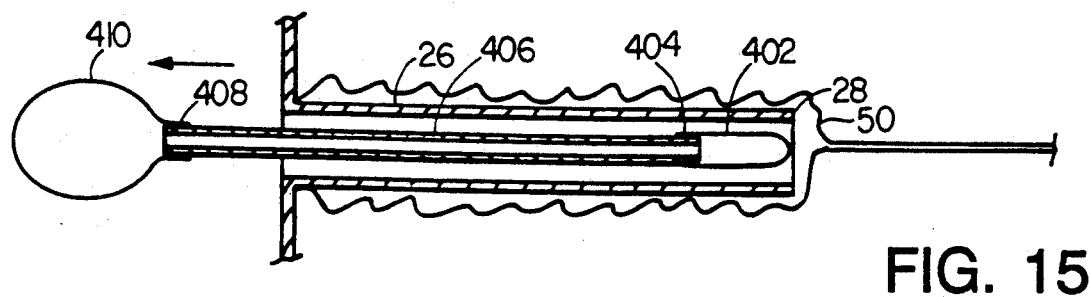

An alternative liner deployment device is shown in FIG. 14. An expandable balloon 402 is removably affixed in sealed relation to one end 404 of a hollow tubular handle 406, and a compressible bulb 410 is removably affixed in sealed relation to the other end 408 of handle 406. The bulb, tube, and balloon are filled with a fluid such as air or water during assembly, so that compression of the bulb results in displacement of the fluid and expansion of the balloon. The tubular handle and the balloon, when deflated, are dimensioned to pass within the guide tube 26. The liner deployment device is inserted, balloon first, through the rear port and through the lumen of the guide tube until the balloon emerges from the end 28 of the guide tube 26. Then the bulb 410 is compressed, expanding the balloon 402 and bringing the balloon into contact with the liner tube 50 (FIG. 14). As the device is moved further frontward, the liner is withdrawn by the balloon from the guide tube. Then the bulb is released, the balloon deflates so that it loses contact with the liner, and the device is withdrawn rearward (FIG. 15). As the device is reciprocally inflated and moved frontward as in FIG. 14 and then deflated and moved rearward as in FIG. 15, while fluid is passed into the container under pressure, the liner 50 is progressively withdrawn from the guide tube 26 as the liner everts.

In a preferred embodiment, tube 406 is made of a polymer such as lucite; balloon 402 is made of an elastomer having a high coefficient of friction with respect to the liner tube, such as latex; and bulb 410 is made of a material such as rubber having sufficient resiliency that when not compressed, it tends to assume its fully inflated configuration. Balloon 402 and bulb 410 are press-fitted over the respective ends of tube 406, and secured if desired with annular clamps.

Referring to FIG. 8, in an alternative guide tube arrangement, the tube storage support may be topologically situated toward that surface of the tube which is contacted by the everting fluid, so that increased pressure of the everting fluid lifts the stored tubing away from the storage support and reduces the frictional resistance of the tubing with the storage support. In this embodiment, the liner emplacing apparatus includes a generally cylindrical housing 200 having cylindrical wall 202, front end face 204, and rear end face 206. Port 203 in front end face 204 is surrounded by nozzle 220 over which introducer tubing 262 is tightly affixed, and port 205 in rear end face 206 is surrounded by internal flange 207. Situated generally transversely within cylindrical container 200 are front bulkhead 214, which is provided with port 222; rear face port 205, bulkhead port 222, front face port 203, and front nozzle 220 are generally axially aligned. Fluid conduit 246 connects fluid input port 248, provided in rear face 206, to fluid input port 244, provided in bulkhead 214, so that fluid can be conducted from outside housing 200 to a chamber 230, which is enclosed between front face 204 and bulkhead 214. Bulkhead 214 is affixed in sealed relation to cylindrical wall 202. Projecting rearwardly from rear bulkhead port 222 toward and generally aligned with rear face port 205 and flange 207 is tube storage support 292.

Flexible tube 250 is made ready for emplacement in the colon by drawing one end 252 of tube 250 over storage support 292, affixing end 252 of tube in sealed relation upon storage support 292 near bulkhead 214, and gathering the major portion 254 of tube 250 over storage support 292; passing the other end 256 of tube 250 through the space 294 enclosed by storage support 292, through bulkhead port 222, and through the lumen of nozzle 220; and turning the other end 256 of tube 250 inside out and mounting it tightly over the free end 221 of nozzle 220. An end 260 of introducer tube 262 is slipped over tube end 256 so that tube end 256 is tightly held between end 260 of introducer tubing 262 and end 221 of nozzle 220.

Now, as described above with reference to FIGS. 2 and 3, introducer tubing 262 is inserted into the anal canal (not shown), and eversion of the flexible tubing into the colon is effected as follows. A stopper 300 is placed into rear face port 205, and chamber 230 is filled with fluid by introducing the fluid into chamber 230 by way of rear fluid input port 248, conduit 246, and fluid input port 244. Here, however, as the fluid fills chamber 230, the stored portion 254 of tube 250 is lifted by fluid pressure away from storage support 292; and pressure of the tube against storage support 292 is prevented. As chamber 230 becomes filled with the fluid the pressure of additional fluid causes tube 250 to begin to evert at everting margin 270. Stopper 300 prevents eversion of the tube in a rearward direction; that is, no everting margin advances in a direction along tube 250 away from tube end 252. As further fluid is introduced by way of rear fluid port 244 into chamber 230, and as tubing 250 continuously everts, everting margin 270 advances as described above in a forward direction proximally within the colon, forming an outer liner tube 272 and continually drawing the stored portion 254 of tube 250 off from storage support 292 around annular end 293 of storage support 292 through the space 294 enclosed by storage support 292, through bulkhead port 222, and through front face port 203, nozzle 220, introducer tubing 262, and outer liner tube 272.

When eversion of tube 250 has proceeded to the desired point, the source of fluid to fluid input port 244 is removed and the fluid allowed to drain out from chamber 230 by way of conduit 246 and fluid input port 248. This permits inner liner tube 274 of everted tube 250 to collapse upon outer liner tube 272 of everted tube 250. Then stopper 300 is removed from rear face port 205, and the colonoscope can now be introduced through rear face port 205, and through the lumen 276 formed by inner surface of inner liner tube 274 of everted tube 272, sliding along lumen 276 of the fully everted liner.

Other embodiments are within the following claims.

Other liner materials can be used, such as natural and synthetic rubber, silicone rubber, polyethylenes, segmented polyurethanes, polyolefins such as polyethylene and polypropylene, copolymers of ethylene or propylene and vinyl acetate, polyvinyl chloride or copolymers of vinyl chloride and the like. The tubing can be reinforced using, for example, materials such as synthetic fibers or threads derived from cotton, silk, nylon, polyester, and the like.

Other lubricants can be used, such as water alone, water containing hydroxyethylcellulose (for example, Natrosol ®) or other water "thickners" such as other cellulose derivatives and glycerine, water containing a surfactant or a mixture of surfactants, or mineral or vegetable oil.

The dimensions of the liner can be selected to adapt the apparatus for human pediatric use, as well as for veterinary uses in any of various mammals. It will be appreciated that the liner can be used to facilitate insertion of instruments other than a colonoscope and to facilitate insertion of instruments such as, for example, endoscopes, into body passages other than the colon. A liner tube having a diameter about ⅜ inch and a length at least 80 inches, as described above, can form an everted liner having a length at least 30 inches when fully everted within the intestine using a liner emplacement device as described above, suitable for colonoscopy in an adult human. A shorter liner tube having a diameter about ⅜ inch can form a liner having an everted diameter as described for colonoscopy and an everted length about 12 inches, suitable, for example, to facilitate insertion of a sigmoidoscope.

Once the liner has been emplaced and the colonoscope has been fully inserted, it can be preferably to withdraw the liner and the colonoscope concurrently.

Figure 16:
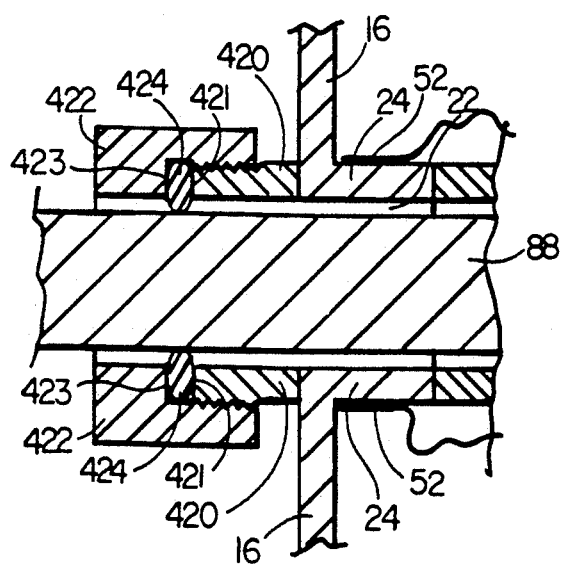
FIG. 16 is a sectional view of a clamp for removably clamping the colonoscope to an emplacement device.

A clamp is shown in FIG. 16 for removably affixing the colonoscope to the container at the rear port, so that withdrawal of the container away from the patient can effect withdrawal of the liner and the colonoscope together. In this embodiment a threaded rearwardly projecting external flange 420 is provided at rear port 22, onto which a threaded nut 422 can be affixed. A compressible O-ring 424 is held between a rearward surface 421 at the end of flange 420 and a frontward surface 423 of nut 422, so that O-ring 424 can be compressed when nut 422 is turned as flange 420, pressing O-ring 424 against the surface of colonoscope 88 and clamping the colonoscope concentrically in place.

Fabrication of Another Liner

Figure 18:
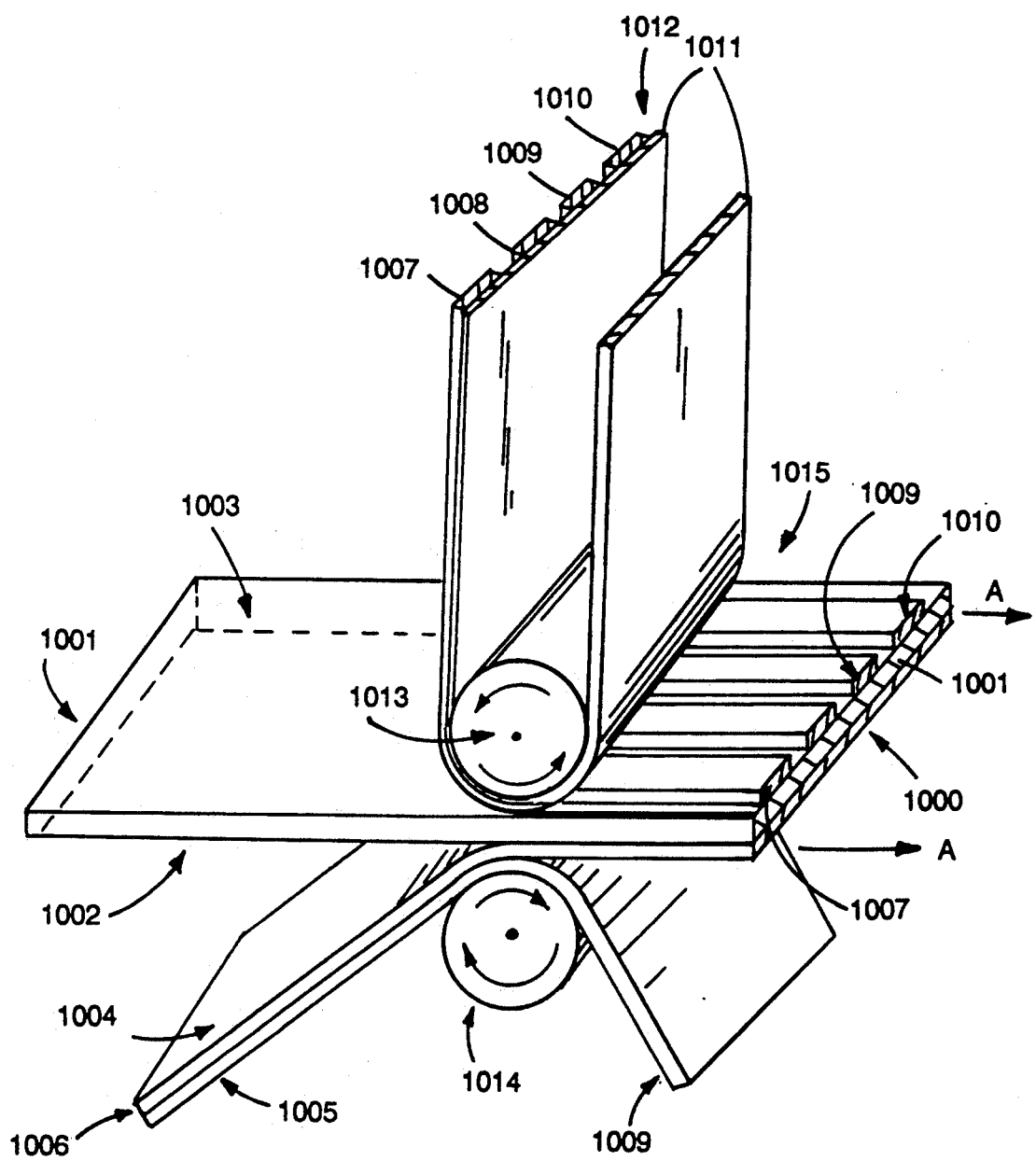
FIG. 18 shows laminating polyurethane with PVP.
Figure 19:
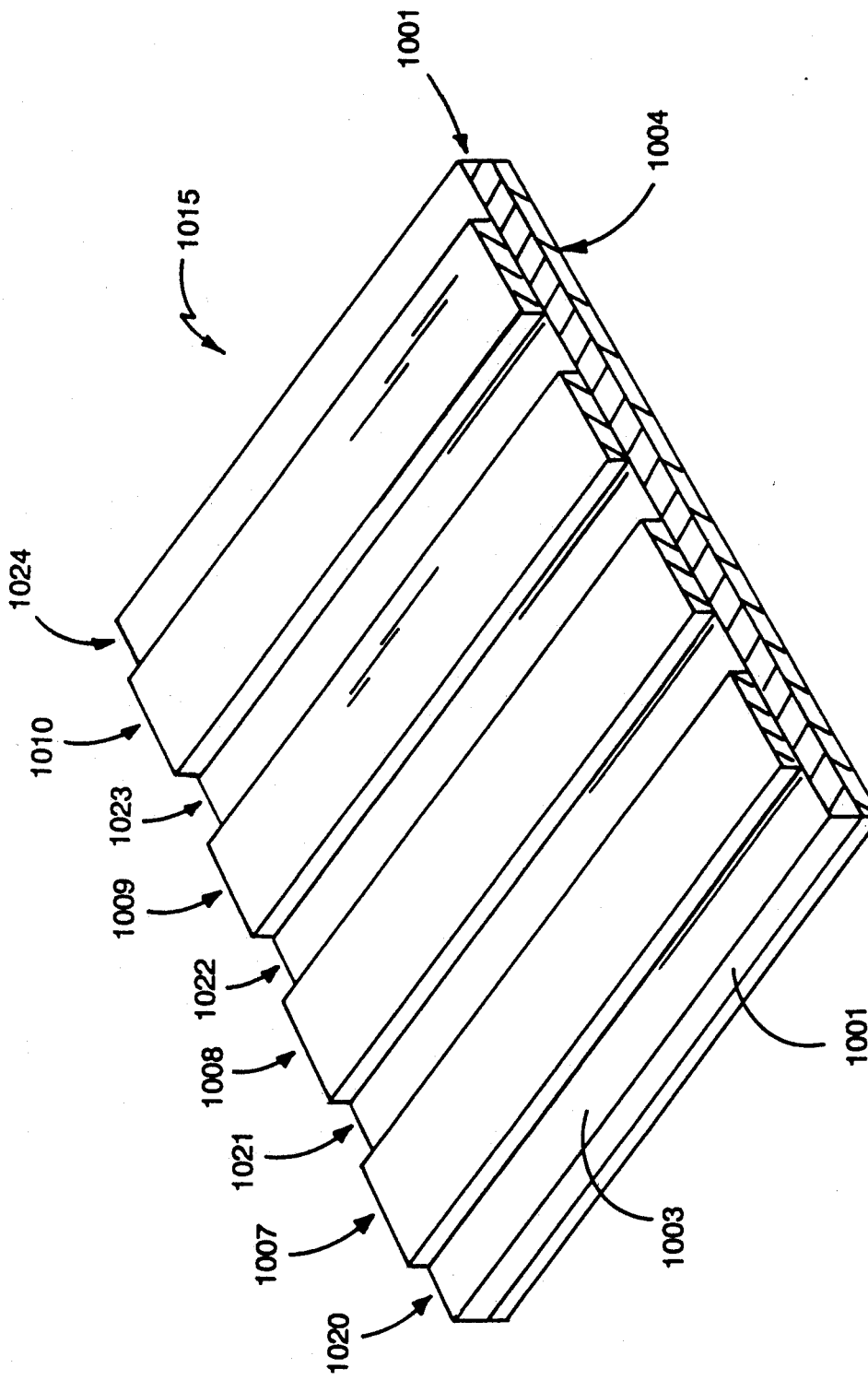
FIG. 19 is a perspective view of a section of a laminated sheet.

Referring to FIGS. 18 and 19, a film (a sheet or layer) 1001 of polyurethane (an elastomeric material), is laminated with lubricous coatings (layers) 1004 and 1007-1010 of polyvinylpyrrolidone (PVP) by applying heat and pressure between film 1001 and coatings 1004 and 1007-1010 with heated rollers 1013, 1014. PVP is a linear polymer which forms a lubricous coating on the polyurethane when wet, The resultant laminated polyurethane-PVP sheet 1015 is then formed (in a manner discussed in detail below), into multiple tubes each of which will serve as an everting liner and has interior and exterior surfaces of PVP. The tubes are sufficiently thin, pliable, and slippery to be used in endoscopy, and yet rugged enough to withstand the puncture forces that are apt to be applied during use.

The PVP surfaces of the laminated tubes are quite lubricous, particularly when exposed to water during emplacement of the liner (as discussed below), thereby facilitating both the emplacement of the tube into the colon and the insertion and manipulation of the colonoscope within the liner. The PVP coatings are durable and do not deteriorate or peel off in storage or during use, and because the PVP is laminated to the polyurethane, the everting liners include no adhesive to possibly harmfully interact with body tissue during use. Although some of the PVP will dissolve in water during use, the lamination procedure embeds sufficient PVP in the polyurethane surfaces to maintain lubricousness throughout the colonoscopic procedure. The durability of the coating (i.e., its resistance to removal by dissolution in the presence of water) can be increased by forming cross-links in the PVP through the application of heat or gamma radiation, as described in detail below.

Moreover, solvents are not relied upon to adhere the PVP to the polyurethane. Solvents, which work by dissolving the uppermost portions of the polyurethane to cause molecules of PVP and polyurethane to intermingle, may weaken the polyurethane and may not uniformly affect the entire surface of the polyurethane film. By contrast, the application of heat and pressure between the PVP and the polyurethane sheets is easily controlled to be quite uniform. And the use of a pair of rollers 1013, 1014 assures that the heat and pressure is applied relatively quickly, thereby inhibiting weakening and stretching of the polyurethane sheet 1001.

Polyurethane film 1001 is 5.0 mils thick to enable the everting liners formed from sheet 1015 to be easily everted, but film 1001 may have any suitable thickness, for example, between one mil and 10 mils. The length and width dimensions of film 1015 depend respectively on the desired lengths of the everting liners to be formed and on the number of liners to be made from one sheet.

PVP coating 1004 is continuous and covers the bottom surface 1002 of polyurethane film 1001. PVP coating 1004 (and coatings 1007-1010) should be thin enough to have minimal effect on the pliability of polyurethane film 1001, and thick enough to render the surface of sheet 1015 lubricous when wet and resist being washed completely away when exposed to water during use or while in storage. PVP coatings as thin as 0.08 mils can be deposited using the laminating technique described herein, but the PVP coatings can be thicker (e.g., 0.5 mils or higher, but preferably between 0.1 mils and 0.2 mils), as desired.

Before being fed between rollers 1013, 1014, PVP coating 1004 is deposited on a separate release paper 1005 of polyester or cellulose using a rotogravure coating machine. In the rotogravure coating machine (not shown) PVP dissolved in any suitable solvent is "painted" onto the release paper using a roller partially immersed in the PVP-solvent solution. The solvent then evaporates, leaving the release paper coated with PVP. Release paper 1005 serves to support the thin PVP coat 1004 prior to lamination and is precoated with silicone 1006 prior to depositing PVP coating on paper 1005 to ease the transfer of the PVP from paper 1005 to polyurethane film 1001.

PVP coatings 1007-1010 are configured as parallel stripes laminated onto upper surface 1003 of polyurethane film 1001. PVP stripes 1007-1010 are, like coating 1004, deposited on a release paper 1011 using a rotogravure coater prior to lamination. Release paper 1011, like paper 1005, is treated with silicone 1012 to assist in the transfer of PVP stripes 1007-1010 to polyurethane film 1001.

Polyurethane film 1001 and PVP-coated release papers 1005, 1011 are advanced together between rotating nip roller 1013 and rotating nip roller 1014 in the direction indicated by arrows A. Nip rollers 1013, 1014 may be coated with Teflon ® to assist in the smooth passage of the sheets between them. Nip rollers 1013, 1014 are between about three inches and five inches in diameter and are configured to apply approximately 75 pounds per lineal inch of pressure to release papers 1005, 1011 and polyurethane film 1001. Rollers 1013, 1014 are heated to a temperature (e.g., between about 290 degrees and 320 degrees Fahrenheit, preferably approximately 310 degrees Fahrenheit) sufficient to cause slight softening of the polyurethane. As release papers 1005, 1011 and polyurethane film 1001 pass through the rollers 1013, 1014, PVP coating 1004 intermixes with polyurethane on lower surface 1002 of film 1001 in response to the heat and pressure applied by nip rollers 1013, 1014, and is thereby mechanically bonded to the polyurethane. Likewise, PVP stripes 1007, 1008, 1009, and 1010 are securely laminated to the polyurethane on upper surface 1003 of film 1001.

If needed, for example if lower laminating temperatures are used at rollers 1013, 1014 to protect release papers 1005, 1011 from damage, PVP-coated polyurethane sheet 1015 can be passed between a downstream pair of rollers heated to, e.g., 310 degrees to 320 degrees Fahrenheit.

We have found that even if rollers 1013, 1014 are at a lower temperature, PVP coating 1004 and stripes 1007–1010 adhere sufficiently to polyurethane sheet 1001 to allow sheet 1015 to be stored without the PVP peeling off. The mechanical bond may not be durable enough to prevent the PVP from washing off (e.g., with water), such a durable bond can be produced by subsequently "baking" sheet 1015 (e.g. at 290 degrees to 320 degrees Fahrenheit for one hour).

In addition, the solubility of the PVP is significantly reduced if PVP-coated sheet 1015 is "baked" at high temperatures (e.g., 290 degrees to 320 degrees Fahrenheit) for a period of time (e.g. two hours), even if the aforementioned high temperatures are applied to rollers 1013, 1014 during lamination. It is possible that this process slightly cross-links the polymerized PVP, thereby reducing its solubility and therefore reducing even further the possibility that the PVP will wash away during use (we have observed a slight color change in the PVP, indicating that some cross-linking has occurred). It is preferable to "bake" the sheet in air (rather than in an inert atmosphere) to assist in the cross-linking. Care should be taken that the baking temperature not be so high as to cross-link the PVP to such an extent as to retard its water lubricity. Also, an everting liner made from sheet 1015 and the liner emplacement device are sterilized together, such as by exposing them the 2.5 Mrad gamma radiation. But the dose should not be too high, because the gamma radiation will further cross-link the PVP.

PVP stripes 1007–1010 are each approximately 2.25 inches wide and are separated on surface 1003 by uncoated regions 1020–1024 of polyurethane, each of which is approximately one inch wide. As described in detail below, polyurethane regions 1020–1024 are left uncoated with PVP so that PVP coated liners may be fabricated from laminated sheet 1015 by sealing various uncoated polyurethane regions 1020–1024 together along their lengths, as described in detail below. Of course, laminated sheet 1015 may include more or fewer than four PVP stripes 1007–1010.

Figure 20:
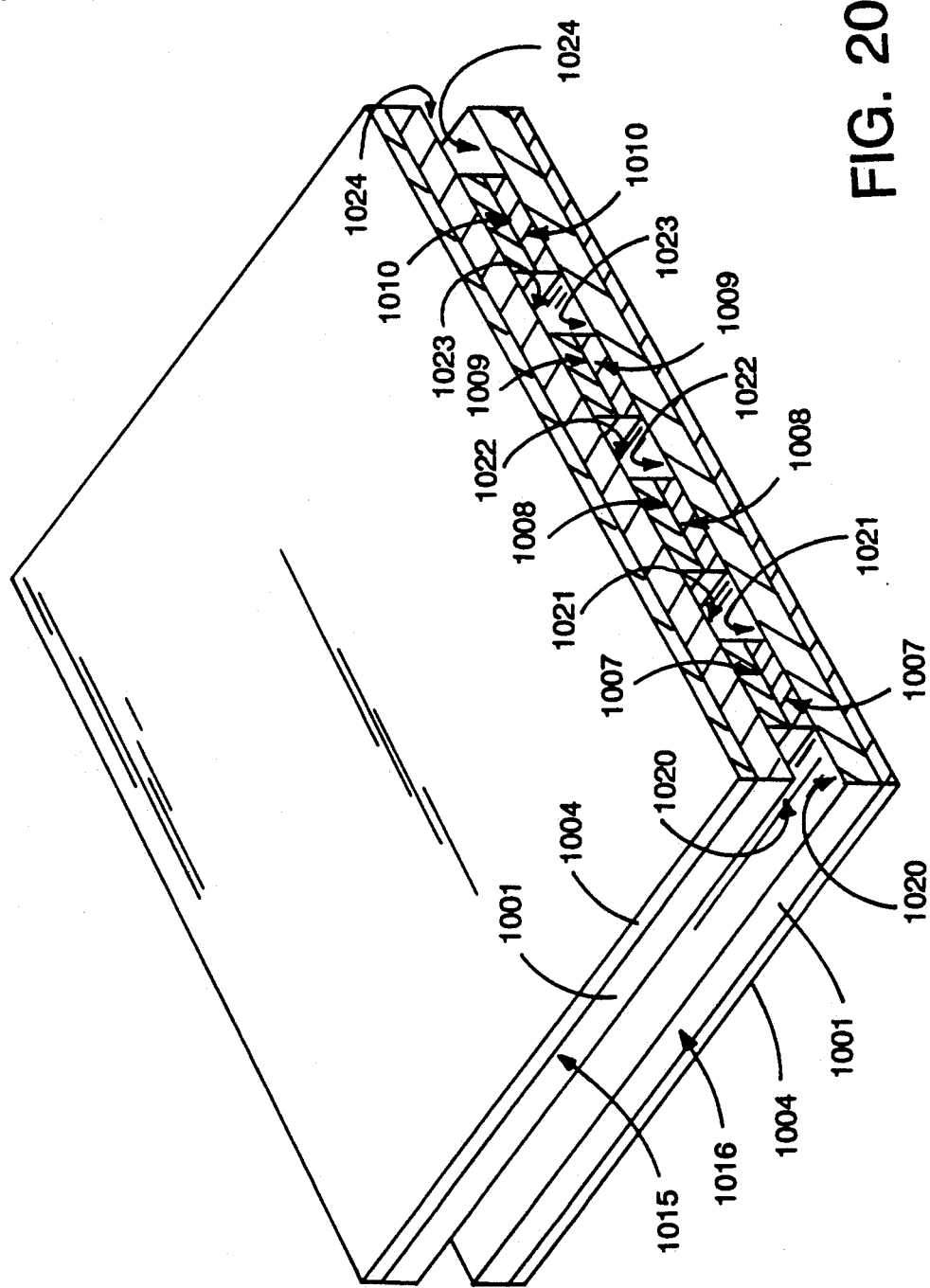
FIG. 20 is a perspective view of sections of two laminated sheets like the sheet shown in FIG. 19, in face-to-face contact.

Referring to FIG. 20, to form liners, two identical laminated PVP-polyurethane sheets 1015, 1016 are placed face to face to form sandwich-like structure. The respective PVP stripes 1007–1010 of the two sheets 1015, 1016 are aligned. Likewise, uncoated polyurethane regions 1020–1024 of the pair of laminated sheets face each other and are parallel to each other along the length of sheets 1015, 1016.

Figure 21A:
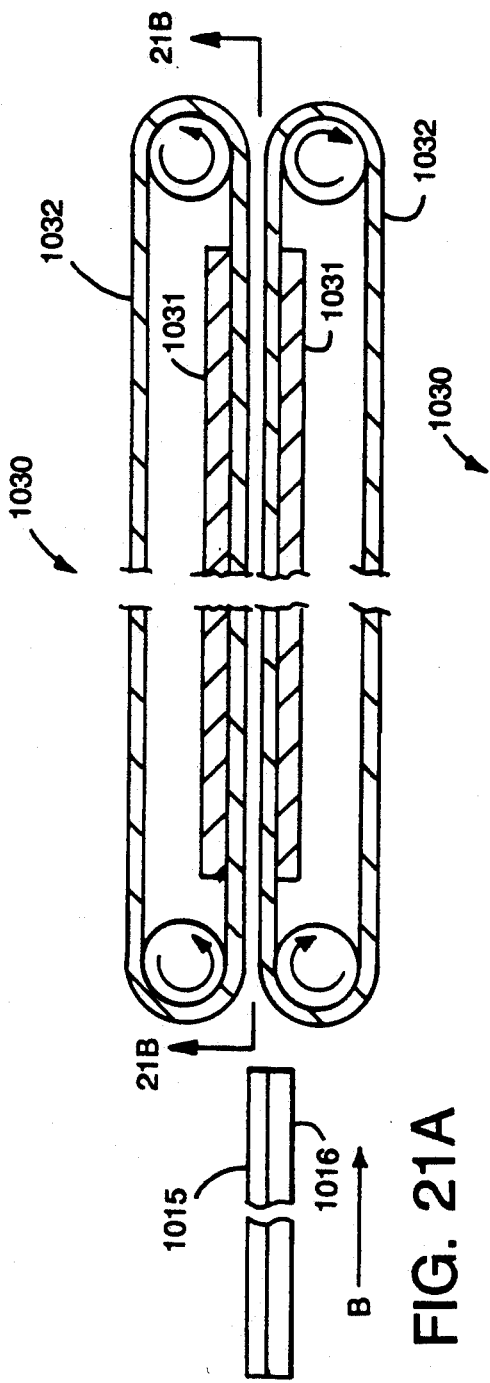
FIGS. 21A and 21B show a heat sealer for sealing together the laminated sheets of FIG. 20.
Figure 21B:
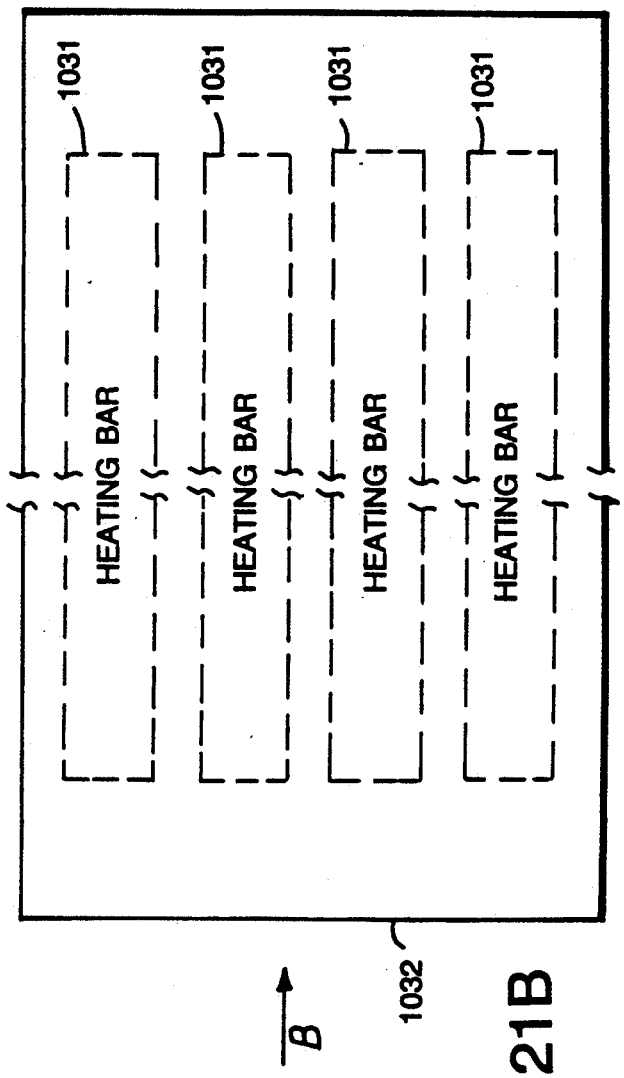
Figure 21C:
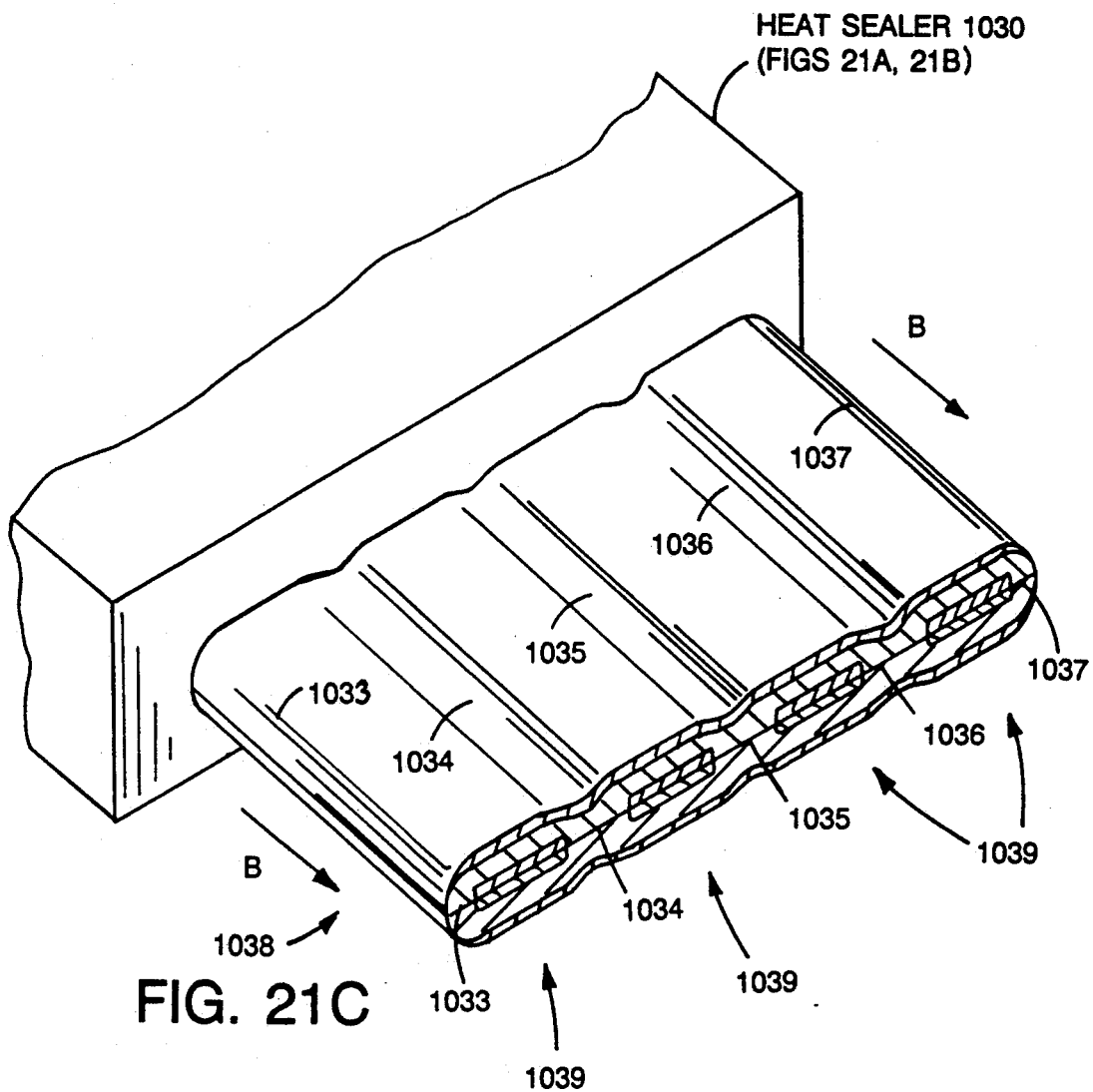
FIG. 21C shows the sealed sheets emerging from the heat sealer.

Referring to FIGS. 21A–21C, the pair of opposing, laminated sheets 1015 are advanced in the direction of arrows B through a heat sealer 1030 to adhere sheets 1015, 1016 together along uncoated, parallel polyurethane regions 1020–1024. Heat sealer 1030 is shown schematically in FIGS. 21A and 21B and includes two overlayed sets of heating bars 1031 which are stationary and aligned with the parallel polyurethane regions 1020–1024 (FIG. 20). Sheets 1015, 1016 are advanced through heat sealer 1030 by a pair of teflon belts 1032 rotated as shown by rollers. Teflon belts 1032 are shown separated from each other in FIG. 21A for clarity, but in use they are pressed into contact by heating bars 1031. The temperature of heated bars 1031 (e.g., between approximately 250 degrees and 350 degrees Fahrenheit) is conducted through belts 1032 into uncoated polyurethane regions 1020–1024 as they are forced into contact with each other (at a pressure of, e.g., 2 psi) by opposing bars 1031. The combined heat and pressure seals regions 1020–1024 together along respective continuous heat seals 1033, 1034, 1035, 1036, and 1037 as sheets 1015 are passed through heat sealer 1030. The PVP stripes do not seal to one another, in part because heat and pressure are not applied between them but also because the PVP-coated polyurethane resists heat sealing.

The resulting double laminated sheet 1038 thus has a series of connected, parallel tube-like liners 1039, each of which defines a passage bounded by a pair of opposing, unattached PVP stripes 1007–1010. Individual liners 1039 are separated by continuous heat seals 1033–1037. The external surfaces of each liner 1039 are coated with PVP.

Figure 22:
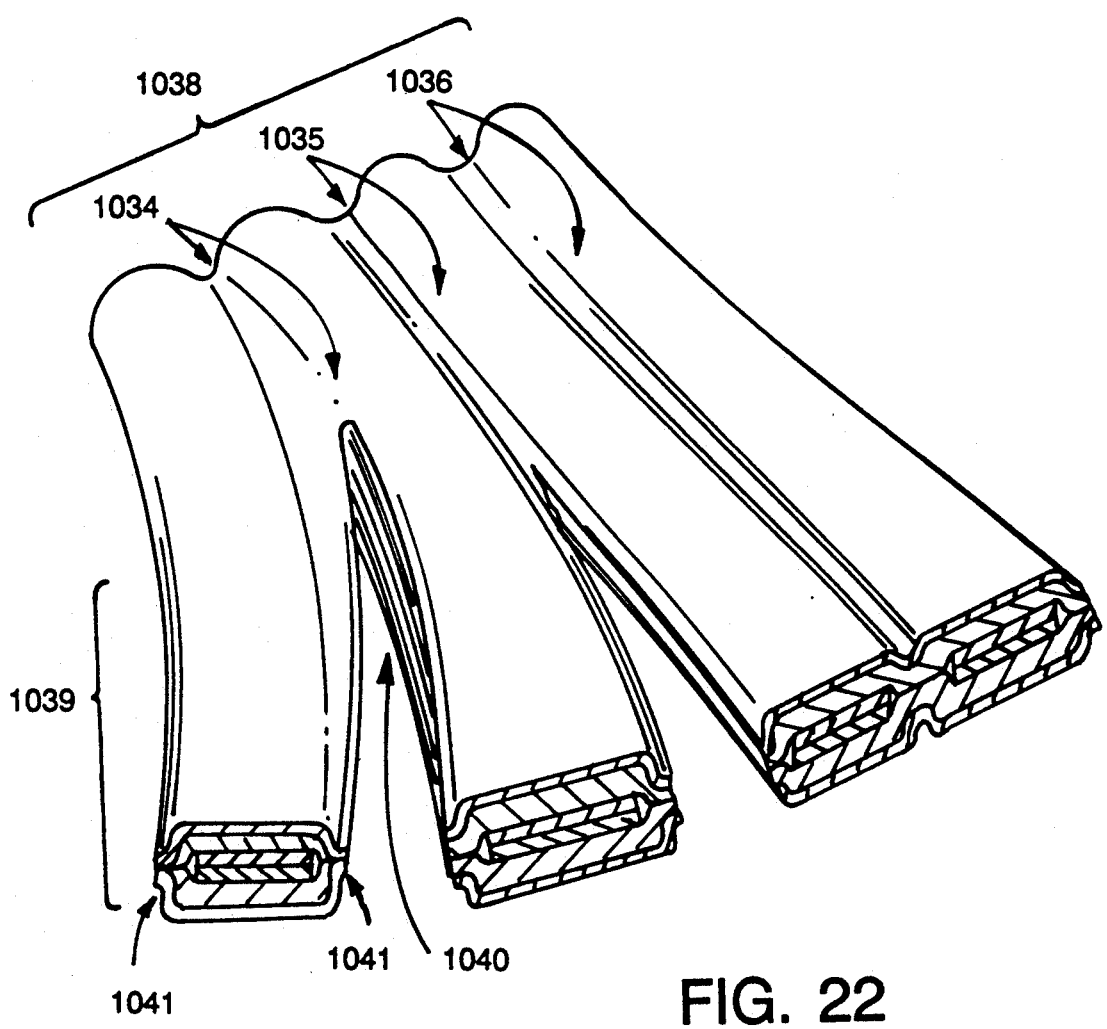
FIG. 22 illustrates cutting the sealed, laminated sheets of FIG. 21C to form evertible liners.

Referring to FIG. 22, liners 1039 are separated from each other by cutting sheet 1038 along the lengths of seals 1033–1037 using rotary knives 1040 (only one is shown). Each seal 1033–1037 is cut approximately along its center line. Thus each liner 1039 includes a pair of ridges 1041 which are each approximately one half of the width of an uncoated polyurethane region 1020–1024 On film 1001 (i.e., 0.125 inches). Ridges 1041 extend the length of and are disposed on opposite sides of each liner 1039. (As discussed below, when used in a colonoscope, liner 1039 is everted so that its ridges 1041 are not exposed to the colon.)

Figure 23:
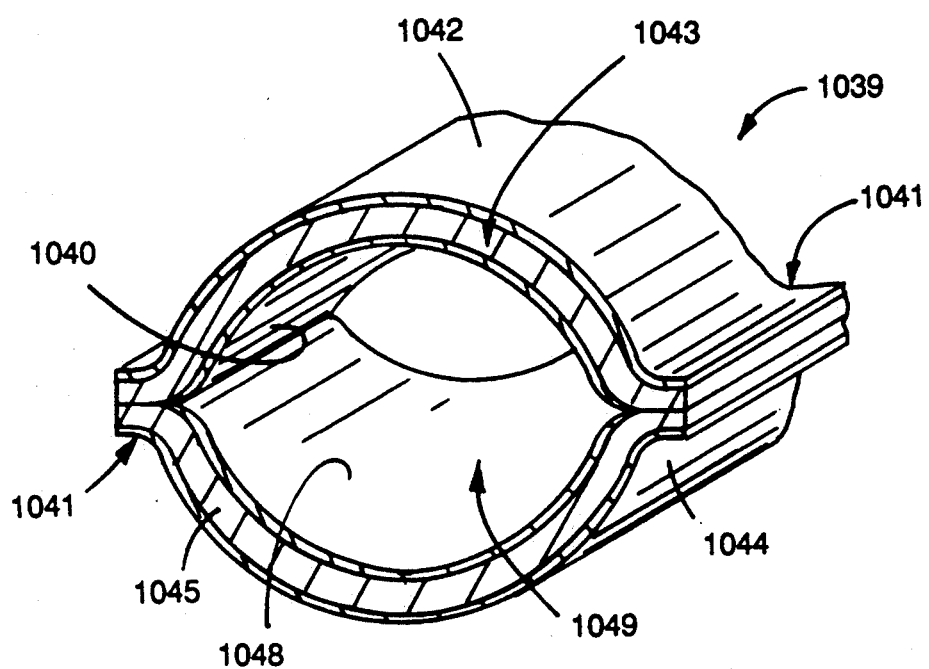
FIG. 23 is an enlarged perspective view of a section of one of the liners of FIG. 22.

Referring to FIG. 23, the exterior surfaces 1042, 1044 and the interior surfaces 1046, 1048 of liner 1039 are PVP coated and thus are lubricous when exposed to water. These PVP coatings enclose regions 1043, 1045 of the polyurethane films 1001 of sheets 1015, and the liner 1039 defines an interior passage 1049. The dimensions of evertible liner 1039 are selected to accommodate apparatus for human pediatric use and for veterinary use with any of various mammals. For example, passage 1049 has a diameter of approximately ⅜ inches, and liner 1039 is at least 80 inches long, prior to eversion, and thus at least 30 inches long when fully everted.

PVP coated liner 1039 can be used with any of the emplacement devices described in this specification.

PVP coating 1004 and stripes 1007–1010 may be laminated in steps rather than at once. For example, film 1001 and release paper 1005 would first be applied through a set of constant diameter rollers to laminate PVP coating onto surface 1002, and then this sheet would be passed through the nip rollers to laminate PVP stripes 1007–1010 onto surface 1003.

Other elastomeric materials, such as flexible vinyl, natural rubber, or nitrile rubber, may be used in place of polyurethane. The PVP may be replaced by alternative lubricous materials, for example a silicone or fluorocarbon.

Figure 24A:
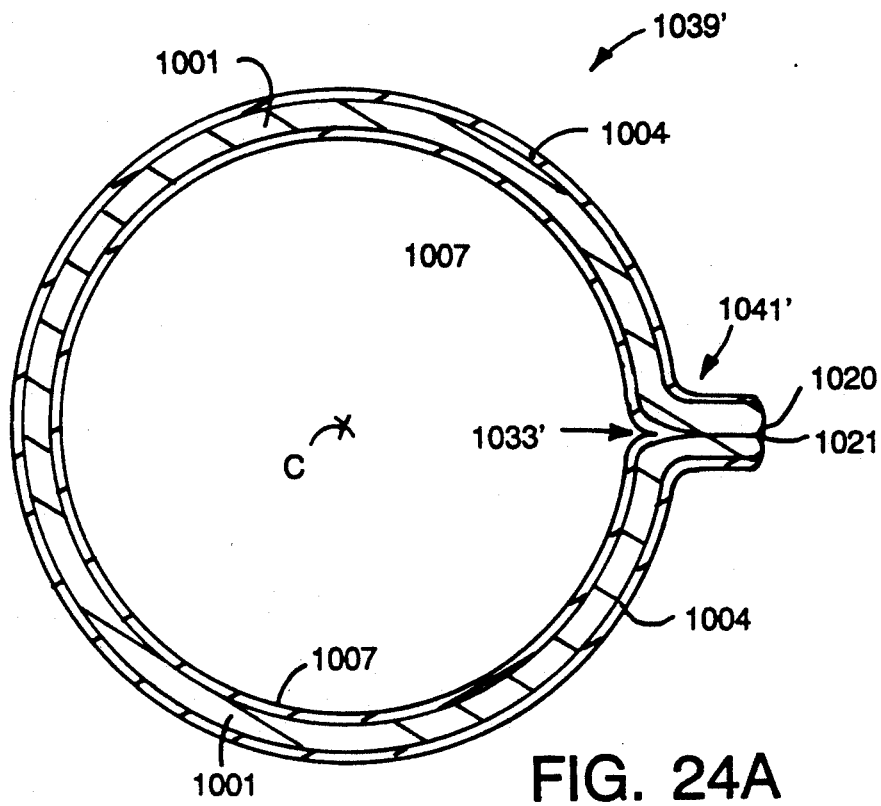
FIGS. 24A and 24B are cross-sectional views of the laminated sheet of FIG. 23 sealed in alternative ways to form a liner which can be emplaced into the body with any of the liner emplacement devices of the invention.

Referring to FIGS. 19 and 24A, everting liners 1039 can alternatively be formed from a single PVP-polyurethane laminated sheet 1015. Sheet 1015 is cut lengthwise (e.g., by rotary knives, not shown) along the centers of uncoated polyurethane regions 1021–1023 to form a series of strips, each of which includes a PVP stripe (e.g., PVP stripe 1007) on one surface and PVP coating 1004 on the other surface. Each strip is folded about its longitudinal axis C so that the uncoated polyurethane regions (e.g., regions 1020, 1021), are aligned. The individual, folded strip is then passed through a heat sealer that seals the aligned, uncoated polyurethane regions together to form liner 1039'. Liner 1039' thus includes only a single ridge 1041' along the heat seal 1033' between the uncoated polyurethane regions, rather than a pair of ridges 1041 (see FIG. 23). Because the strip is folded, the width of the PVP stripes should be increased over that used when forming liners 1039 from a pair of face-to-face sheets.

Figure 24B:
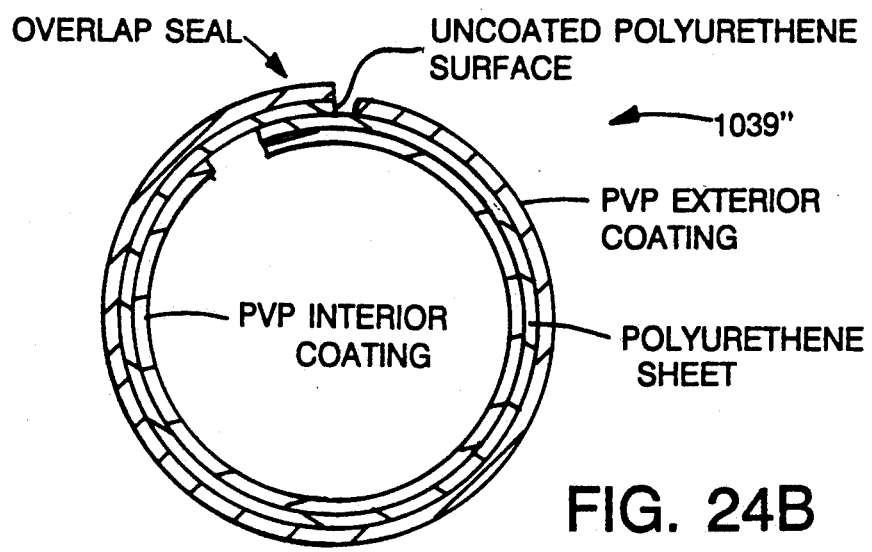

Referring to FIG. 24B, still another way of fabricating everting liner 1039″ from a PVP-coated sheet is with an "overlap" seal. The "interior" and "exterior" PVP coatings are deposited on the polyurethane sheet so that when the laminated sheet is folded about its longitudinal axis a pair of uncoated polyurethane surfaces overlap one another and can be heat sealed together.

If the PVP coatings are made sufficiently thin (e.g., 0.08 mils), it is possible to form liner 1039, 1039′, or 1039″ by sealing the laminated sheets (or strips of the sheets, as discussed in the preceding paragraph) together through the PVP coatings. This would eliminate the need for providing uncoated polyurethane regions.

Alternative Liner Emplacement Modules

Figure 25:
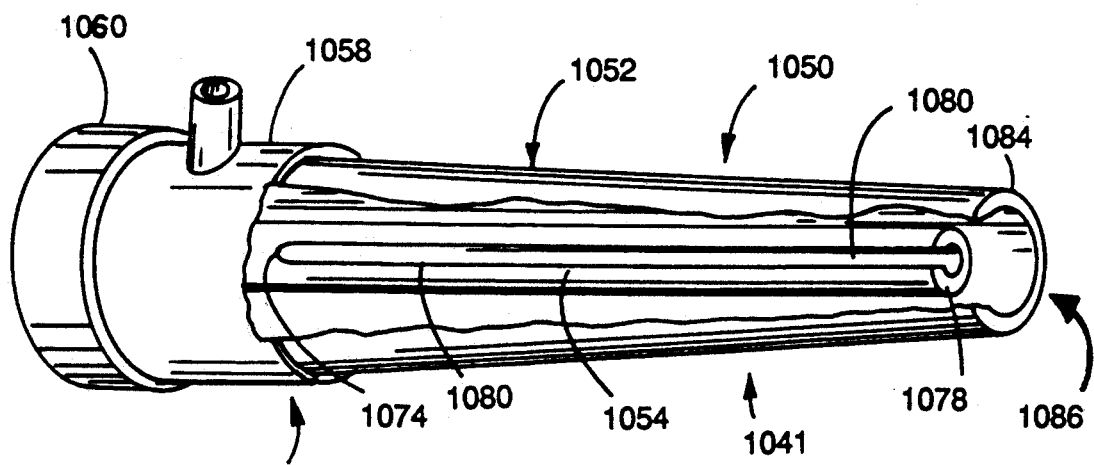
Figure 26:
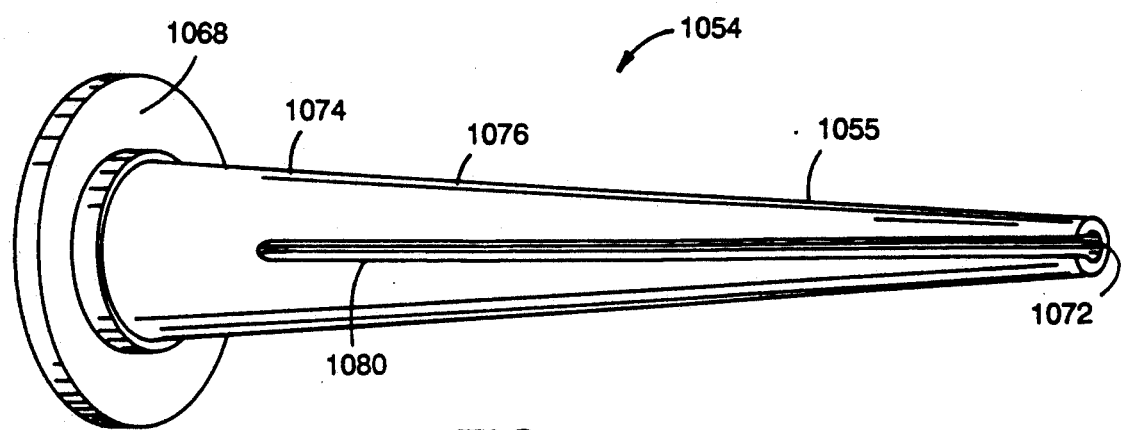

Referring to FIGS. 25-27, another deployment module 1050 for emplacing evertible liner 1039 within the body includes a conical, hollow housing 1052 within which is mounted a hollow, slotted guide tube 1054 about which the PVP coated liner 1039 (not shown in FIGS. 25 and 26) is gathered. Housing 1052 and its components, including guide tube 1054, are sterile and are made from molded plastic to be disposable. The distal end 1056 of housing 1052 (i.e., the end positioned furthest away from the patient during use) is secured to a hollow flange 1058 (for example, by gluing or ultrasonic welding).

Referring also to FIG. 27A, a collar 1060 is releasably secured to guide tube 1054 (e.g., by aligning pins 1064 on collar 1060 with axial portions 1066a of slots in flange 1058, sliding collar 1060 onto flange 1058, and then rotating collar 1060 (e.g., by ¼ turn) until pins 1064 become engaged in circumferential portions 1066b of the slots). An O-ring seal (not shown) disposed around flange 1058 provides a tight fit between collar 1060 and flange 1058. Collar 1060 has a recess within which the base 1068 of guide tube 1054 is secured. Guide tube 1054 extends proximally (i.e., toward the patient) from base 1068. Base 1068 is annular and includes an opening 1070 which defines the distal port of module 1050 and communicates with a central, cylindrical bore 1072 within guide tube 1054. The diameter of opening 1070 at base 1068 exceeds that of bore 1072, and opening 1070 narrows in a tapered manner until the diameter equals that of bore 1072 (this occurs at region 1074).

The stem 1076 of guide tube 1054 tapers from a diameter of about 0.375 inches at base 1070 to approximately 0.25 inches at proximal end 1078. The taper both aids in fabrication (e.g., by molding) and assists in the removal of liner 1039 from guide tube 1054 during emplacement. Guide tube 1054 is approximately 9.5 inches long. A straight, rectangular slot 1080 (FIGS. 25, 26) is cut completely through a wall of guide tube stem 1076 to expose bore 1072. Slot 1080 is 0.094 inches wide and extends distally from proximal end 1078 to the point 1074 at which bore 1072 and flared opening 1070 meet (about two inches proximally of base 1068). Slot 1080 thus provides a passage between bore 1072 and the exterior surface 1055 of guide tube 1054 for reasons discussed below. Cylindrical bore 1072 is about 0.125 inches in diameter; the maximum diameter of opening 1070 is approximately 0.2 inches at base 1050.

Housing 1052 also tapers in diameter to a narrow tip 1084 to simplify assembly of the liner into the housing and to keep the dimensions of the module small. The inserter port 1086 defined by tip 1084 is about 0.75 inches to 0.80 inches in diameter (reduced from a maximum diameter of about 1.5 inches where housing 1052 meets flange 1058). The total length of module 1050 (from base 1068 to inserter port 1086) is about 10.625 inches. Thus, the proximal end 1078 of guide tube 1054 lies approximately one inch distally of inserter port 1086. Liner 1039 (FIG. 23) is disposed within a chamber 1053 defined by the interior of housing 1052 and is gathered over guide tube 1054, as shown in FIG. 26. One end 1090 of liner 1039 is tightly mounted to the distal end 1059 of housing 1058, such as by everting liner 1039, sliding it over flange end 1059, and taping it in place. The other end 1092 of liner 1039 is everted and taped to the exterior surface of housing 1050 at tip 1084. Liner 1039 is gathered about guide tube 1054 so that the ridges 1041 (FIG. 23) of liner 1039 face the interior surface of housing 1052. As will be seen, this prevents ridges 1041 from contacting, and possibly irritating, the walls of the colon as liner 1039 is everted and emplaced.

Figure 28:
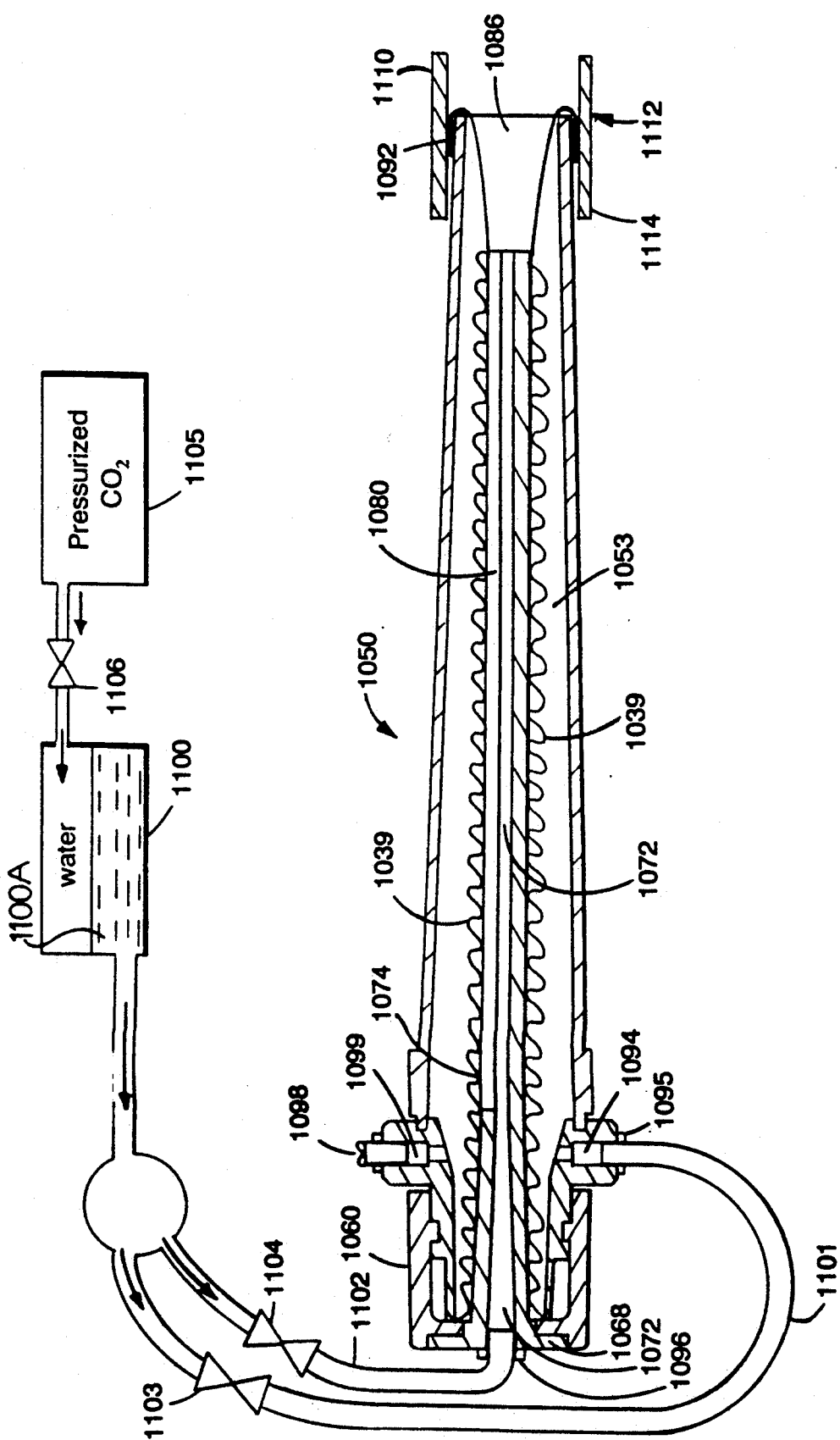
FIGS. 28 and 29 are diagrams useful in understanding the operation of the emplacement devices of FIGS. 25-27.
Figure 29:
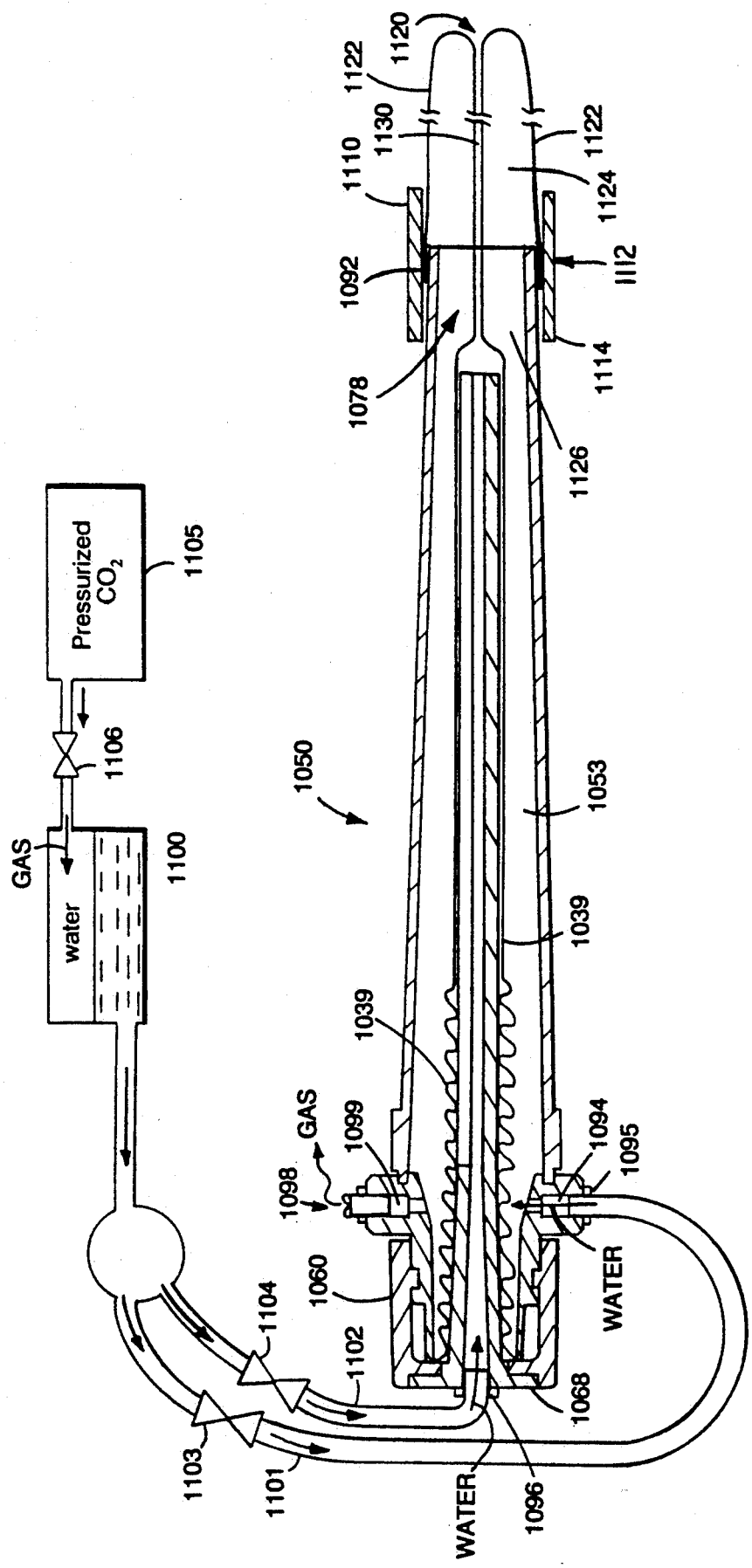

Referring to FIGS. 28 and 29, the procedure for emplacing liner 1039 by eversion into the colon is as follows. Module 1050 is connected to a reservoir 1100 of fluid, such as water 1100a. A water inlet 1094 for housing chamber 1053 is connected via fitting 1095 and tubing 110 to the reservoir. A valve 1103 in tubing 1101 maintains this fluid path closed (as shown in FIG. 28) until the emplacement procedure begins. A similar fluid path is provided from reservoir 1100 to bore 1072 (and slot 1080) in guide tube 1054, via tubing 1102 and a fitting 1096 inserted into opening 1070 in base 1068. A normally closed valve 1104 regulates the flow of fluid through this path and is shown closed in FIG. 28. Tubings 1101, 1102 are each medical grade Tygon® tubing. A gas relief valve 1098 mounted in fitting 1099 allows air to escape from chamber 1053 as water is introduced into the housing during emplacement.

An end 1110 of bridge tube 1112 is inserted into the anus to provide a passageway for inserter port 1086. Inserter port 1086 is placed into the exposed end 1114 of bridge tube 1112. Bridge tube 1112 provides an unobstructed passage for the emplacement of liner 1039 into the colon and is made of a flexible material, for example latex rubber and is inserted transanally beyond the rectal sphincter. Bridge tube 1112 is sufficiently pliable that it does not cause damage to the tissues of the anus or rectum or undue discomfort to the patient.

The operator begins emplacement by applying pressurized gas (such as $CO_2$) 1105 to reservoir 1100 by selectively opening valve 1106 (which is activated, for example, by a foot switch); and opening either or both of valves 1103, 1104. Pressurizing water 1100a in reservoir 1100 at approximately one to two pounds per square inch (psi) has been found to be sufficient to completely evert liner 1039 into the colon. Water 1100a flows through fitting 1094 into housing chamber 1053, displacing air via relief valve 1098. As water flows into chamber 1053, liner 1039 is pulled off of guide tube 1054 and advanced, inside-out (i.e., everted) into the colon through bridge tube 1112. The flow of water into guide tube bore 1072 and radially out of bore 1072 via slot 1080 helps urge the gathered liner 1039 off of guide tube 1054, thereby assisting in emplacement.

As liner 1039 everts, the margin 1120 of the liner advances in a forward direction proximally within the colon, forming an outer liner tube 1122 that contacts the colon wall and continually draws, as a trailing tube portion 1124, the major stored portion liner 1039 off of guide tube 1054 and out of chamber 1053. As liner 1039 is withdrawn from guide tube 1054, inner surfaces of liner 1039 (i.e., the surfaces that faced exterior surface 1055 of guide tube 1054) form a hollow lumen 1130 that progresses into the colon as liner 1039 everts. By the nature of eversion, there is little or no sliding between outer liner tube 1122 and the inner wall of the colon.

As trailing tube portion 1124 is withdrawn from guide tube 1054, water pressure within housing 1053 (about one to two psi) causes the portion of liner tube 1126 in front of the proximal end 1078 of guide tube 1054 to collapse into a ribbon as it is pulled off of the guide tube. As a result, only a small quantity of water is permitted to flow from guide tube bore 1072 through lumen 1130 and into the colon. This effect can be enhanced by opening valve 1104 only part way, thereby restricting the flow of water into guide tube 1054. (Alternatively, the tip 1072 of guide tube 1054 may be closed.) Liner deployment is monitored by observing the feed of liner 1039 off guide tube 1054 (housing 1052 is made transparent for this purpose) or by measuring the falling water level in water reservoir 1100.

The PVP coating on the interior and exterior surfaces of everting liner 1039 becomes lubricous in response to its exposure to water 1100a from reservoir 1100. The low coefficient of friction of the PVP-coated liner 1039 allows liner 1039 to be emplaced with very low hydraulic pressure from reservoir 1100, even through relatively tight strictures (such as 1 cm or less) in the colon. If smaller constrictions are encountered, valve 1106 may be opened slightly further, to pressurized water 1100a at, e.g., up to 4 psi. However, the pressure should not be increased so much that liner 1039 is caused to balloon in the colon. Even the small amount of water that is allowed to pass into lumen 1130 via bore 1072 is sufficient to cause the surfaces of lumen 1030 to be well lubricated, which facilitates insertion of the colonoscope.

When liner 103 is fully everted, valves 1103, 1104, 1106 are closed, the gas pressure in reservoir 1100 is released, and the water is drained from chamber 1053 and the emplaced liner, for example by opening a valve (not shown) in tube 1101 near inlet 1094. Bore 1072 contains little water, because of the collapse of liner 1039 as it is withdrawn from guide tube 1054, as discussed above.

After the water is drained, tubes 1101, 1102 are removed and collar 1060 is detached from flange 1058 (e.g., by rotating collar 1060 until pins 1064 and axial slots 1066a (FIG. 27, 27A) are aligned, and then sliding collar 1060 off of flange 1058). This also serves to remove guide tube 1054 from housing 1052. Because end 1090 of liner 1039 is attached to the distal end 1059 of housing 1052, the liner is not disturbed as guide tube 1054 is slid out of the open distal end of housing 1052.

Figure 30:
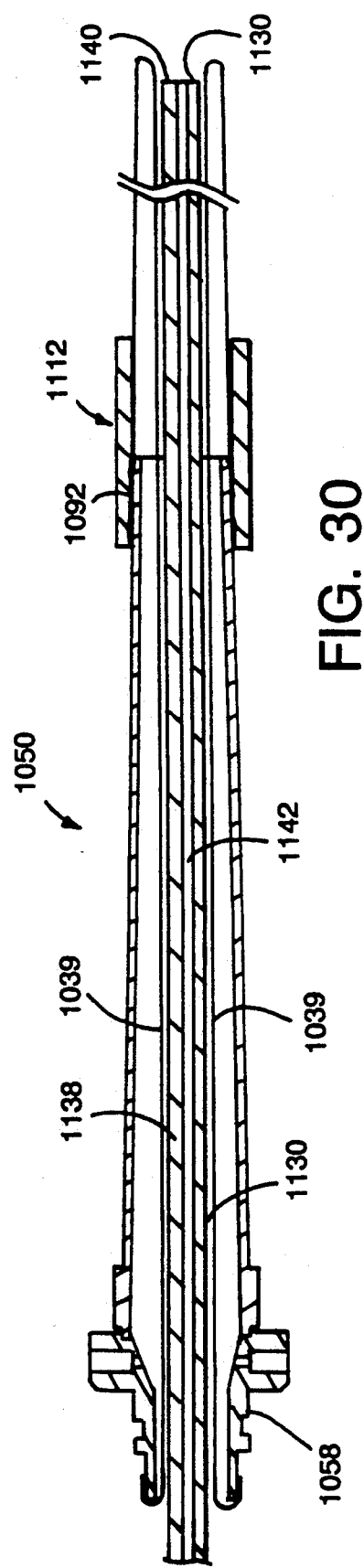
FIG. 30 is a side sectional view of a colonoscope inserted through the liner according to the procedure illustrated in FIGS. 28 and 29.

Referring also to FIG. 30, colonoscope 1138 is inserted into the colon by guiding the tip 1140 of the instrument into lumen 1130 of liner 1039 and sliding colonoscope 1138 through liner 1039. Lumen 1130 is wet (due to the trickle of water that escaped into it through guide tube 1054 during the liner emplacement) and as a result the PVP coating within the lumen is very slippery and readily allows colonoscope 1138 to be passed through it. If additional lubrication is needed, water is injected into lumen 1130 through the tip 1140 of colonoscope 1138 via a passage 1142 in the instrument. Although a small quantity of water is introduced into the colon via guide tube 1054 during liner emplacement, the water does not substantially interfere with the inspection of the colon with colonoscope 1138. If desired, this excess water is easily drained through the interior 1142 of colonoscope 1138 using suction. After the colon has been examined, colonoscope 1138, module 1050, and liner 1039 are withdrawn from the patient.

Referring to FIGS. 31 and 31A, yet another liner insertion module 1200 includes a liner storage housing 1202 which is releasably secured to insertion nozzle 1204. Liner 1039 is gathered about a slotted guide tube 1206 (similar in construction to guide tube 1054) disposed within housing 1202. Housing 1202, nozzle 1204, and guide tube 1206 are disposable plastic parts fabricated by, e.g., injection molding (if so, guide tube may be tapered like guide tube 1054 to ease removal from the mold). The distal end of guide tube 1206 terminates in a base 1212 and an O-ring seal 1208 provides a tight fit between guide tube base 1212 and the distal end 1210 of housing 1202.

A central bore 1232 (about ⅛ inch in diameter) extends through guide tube 1206 from base 1212 to its proximal end. A pair of small holes 1233 in base 1212 (about 3/32 inches in diameter) allow fluid that is introduced into housing 1202 (via an opening 1222 in nozzle 1204) to flow through guide tube 1206 and out longitudinal slot 1234 to urge liner 1039 off of the tube. A constriction 1231 (approximately 0.040 inches in diameter) is disposed in base 1212 between holes 1233 and bore 1232 to restrict the flow of fluid into bore 1232 (and thus into the colon) during liner emplacement. Central bore 1232 is open at the proximal end 1235 of the guide tube, but it may alternatively be closed to further restrict the fluid flow into the colon.

The proximal end 1215 of housing 1202 includes a pair of right-angled slots 1216 (FIG. 31A) that are engaged by a pair of pins 1218 on nozzle 1204. Thus, housing 1202 is fastened to nozzle 1204 simply by inserting proximal end 1215 over the nozzle with pins 1216 aligned with slots 1218, and then twisting housing 1202 clockwise to position pins 1216 as shown in FIG. 31A. An O-ring seal 1219 provides a tight fit between proximal end 1215 and nozzle 1204.

The proximal end 1220 of nozzle 1204 is tapered in diameter to facilitate attachment of the liner at 1226 and to keep the dimensions of the device small (particularly at the end adjacent to the patient). A pair of openings 1222 and 1224 respectively allow water to be injected into module 1200 and gas to be vented during eversion.

Liner 1039 (FIG. 23) is gathered about guide tube 1206. One end 1226 of liner 1039 is everted over an insertion port 1228 of nozzle and taped in place. The other end 1230 of liner 1039 is left unsecured near the distal end 1210 of housing 1202. A washer 1229 disposed about base 1212 forward of holes 1233 prevents the free end 1230 of liner 1039 from clogging the holes.

Figure 32:
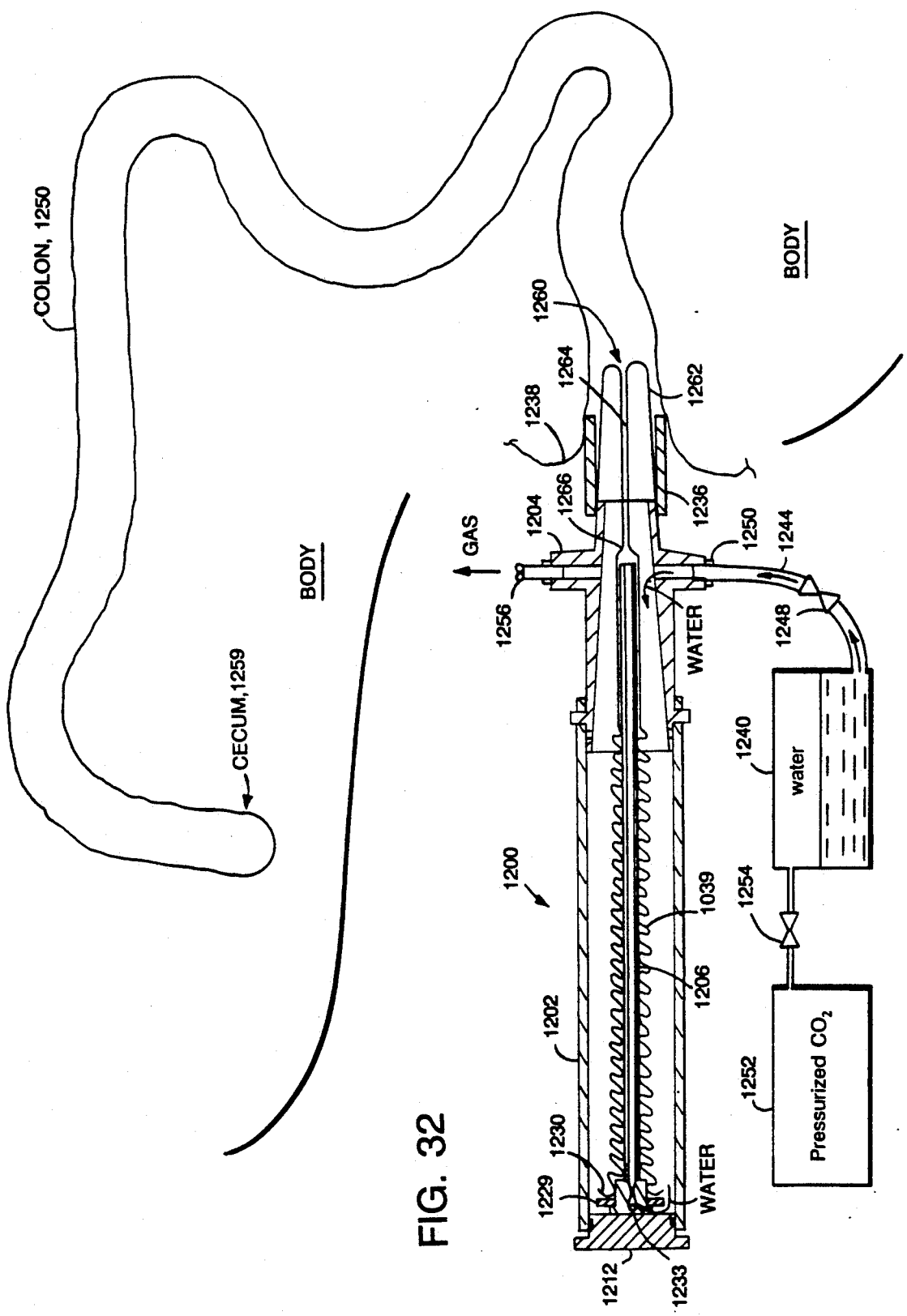
FIGS. 32 and 33 illustrate emplacing a liner into the colon with the device of FIG. 31.

Referring also to FIG. 32, the liner eversion process is similar to that discussed above. Module 1200 is connected to a source of fluid, such as water reservoir 1240, via tubing 1244 and valve 1248. Tubing 1244 is connected to fitting 1250 in nozzle 1204. The insertion port 1228 of nozzle 1204 is inserted into bridge tube 1236, which has previously been inserted transanally beyond the rectal sphincter 1238.

The operator pressurizes the water to about one to two psi by applying pressurized $CO_2$ to reservoir 1240 via valve 1254. Then, valve 1248 is opened, and eversion begins. Air escapes from the interior 1203 of housing 1202 via valve 1256. As before, liner 1039 is pulled off of guide tube 1206 by the injected water and is advanced, inside-out, into the colon 1258. Liner 1039 is eased off of guide tube 1206 by the flow of water through the central bore 1232 (via holes 1233) of tube 1206 and out of slot 1234. As liner 1039 everts, the margin 1260 of the liner advances proximally within colon 1258, forming an outer liner tube 1262 within the colon. As liner 1039 is drawn off of tube 1206, the inner surfaces of the liner form a hollow lumen 1264 that advances within colon 1258 as liner 1039 everts. The water pressure within nozzle 1204 causes liner 1039 to collapse into a ribbon 1266 as it is pulled off of the guide tube, thereby preventing large quantities of water from flowing through lumen 1264 and into the colon.

Figure 33:
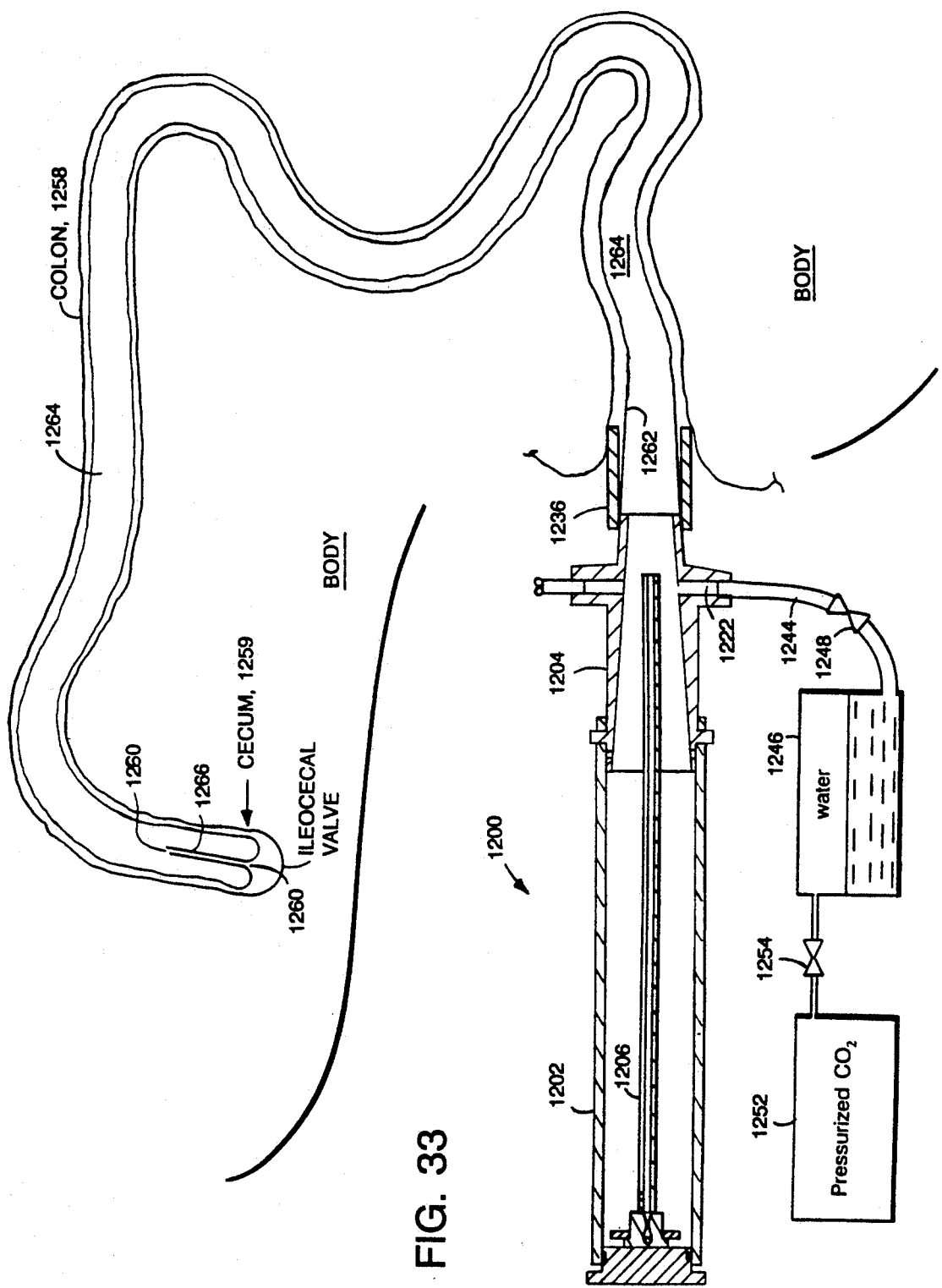

Referring also to FIG. 33, as eversion proceeds the portions of liner 1039 disposed forward of free end 1230 are pulled off of guide tube 1206, and further eversion causes the free end 1230 of liner 1039 to be pulled along and off of guide tube 1206 and into the colon. As a result, further eversion of liner 1039 produces a single-walled outer tube 262 behind free end 1230. The fluid pressure within the everted liner keeps liner free end 1230 collapsed into a ribbon 1266 and prevents a significant amount of water from entering lumen 1264.

Eversion proceeds until liner 1039 is fully emplaced in colon 1258 so that margin 1260 has reached cecum 1259. In most cases the operator will observe that eversion slows down or stops when margin 1260 reaches cecum 1259. But if colon 1258 is weak, the few pounds of water pressure within the everting liner may be sufficient to stretch the colon walls, even after the cecum has been reached. Accordingly, the volume of water used during eversion may be monitored and eversion halted when a predetermined amount of water has been used. The typical adult colon is approximately 120 cm long, and thus with a liner diameter of 0.75 inches approximately 340 cc of water are needed to complete the eversion. Liner 1039 is about 150 cm long to ensure that it reaches cecum 1259.

Figure 34:
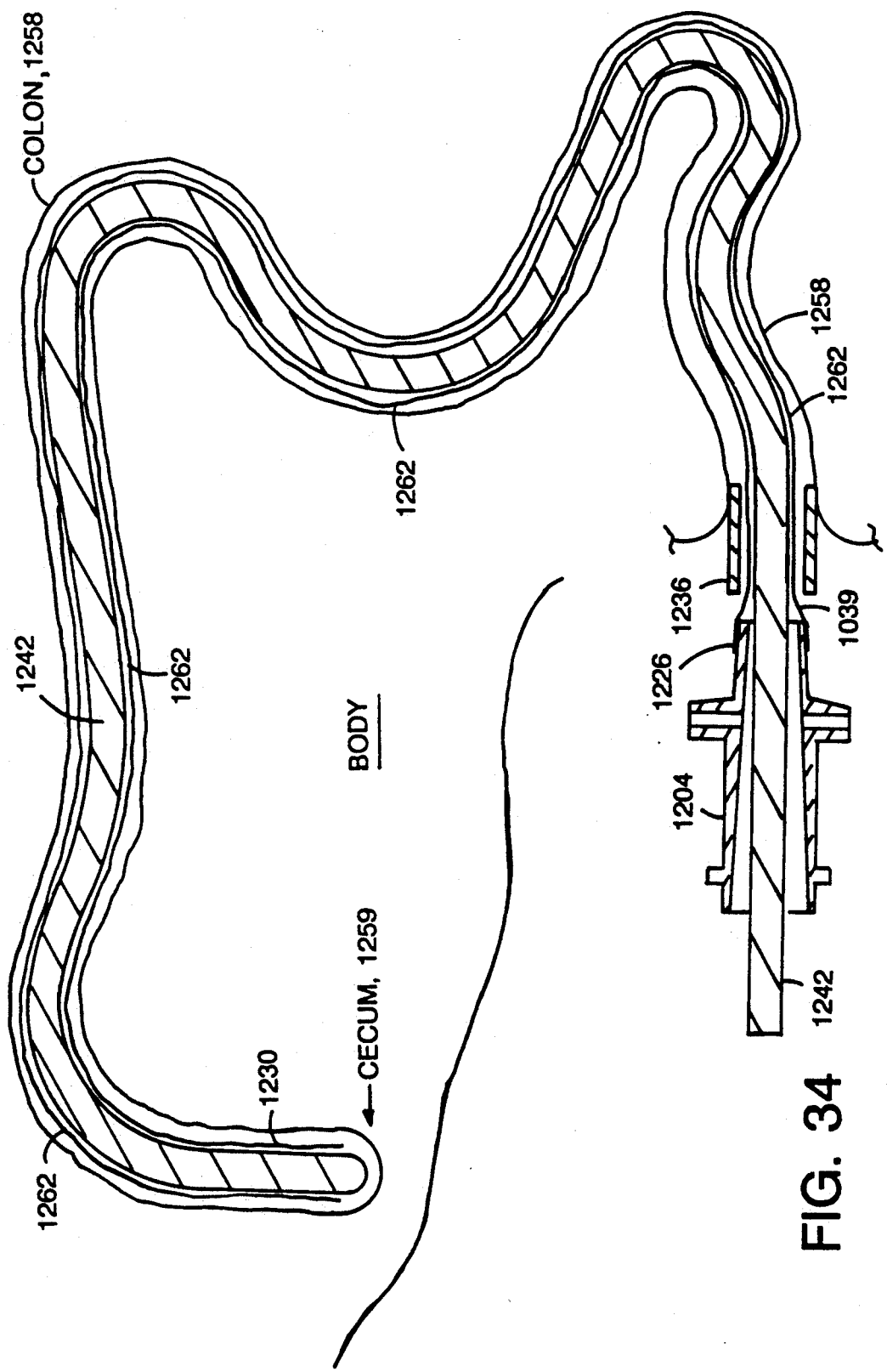
FIG. 34 shows a colonoscope inserted into the colon through a forward part of the liner emplacement device of FIG. 31 after the rearward part of the device has been removed.

Referring to FIG. 34, with eversion complete, valves 1248 and 1254 are closed and tubing 1244 removed from module 1200. Water within the emplaced liner 1039 is drained, for example via opening 1222 in nozzle 1204. Then, housing 1202 and guide tube 1206 are withdrawn together from nozzle 1204 (i.e., by twisting housing and removing pins 1216 from slots 1218, FIG. 31A). Liner 1039 does not extend rearward of nozzle inserter port 1228 and thus does not interfere with the removal of the housing and guide tube.

The absence of housing 1202 (which is approximately 9.25 inches long) leaves only the relatively short nozzle (e.g., four inches long or less) through which colonoscope 1242 need be fed to be inserted into colon 1258. Colonoscope 1242 is advanced through the tube 1262 formed by liner 1039 until the operator observes cecum 1259 through tip of colonoscope 1242 (the colonoscope optics are not shown). The lubricity of the PVP-coated liner facilitates insertion, but if additional lubrication is needed, water can be injected into liner through the colonoscope tip.

When cecum 1259 is observed, the operator slowly withdraws liner 1039 from the colon by pulling nozzle 1204 away from the patient to expose the tip of colonoscope 1242 through the free end 1230 of liner 1039. Inspection of the length of colon 1258 then proceeds by slowly withdrawing colonoscope 1242 and liner 1039 together.

Figure 35:
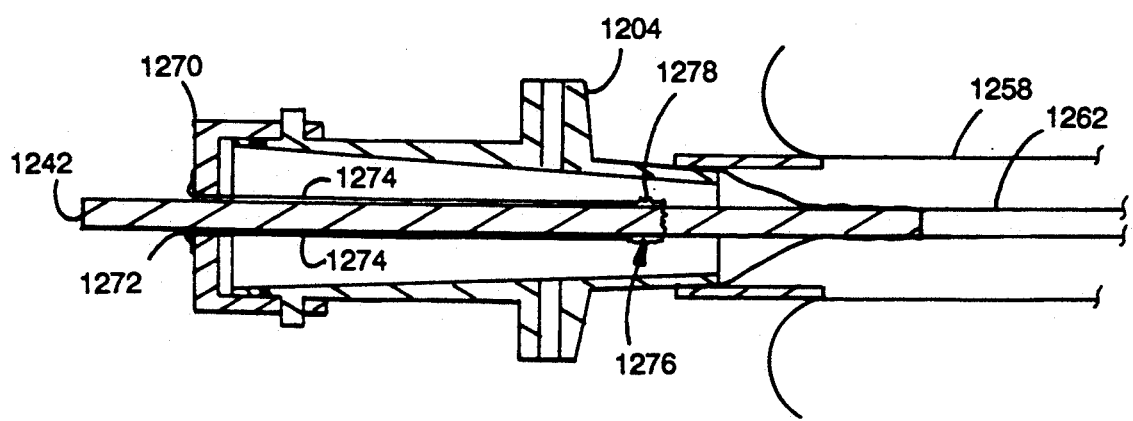
FIG. 35 is a cross-sectional view of an alternative embodiment of the liner emplacement device of FIG. 31.

Referring also to FIG. 35, in some cases it is desirable to examine the portion of the small intestine (not shown) immediately adjacent to cecum 1259 by inserting the colonoscope through the ileocecal valve at cecum 1259. To do so, a fitting 1270 is secured to nozzle 1204 in the same way that housing 1202 was attached to nozzle 1204 (i.e., by engaging a pair of slots on fitting 1270 in pins 1218 (FIG. 31A) and rotating fitting 1270 clockwise with respect to nozzle 1204). Fitting 1270 includes an opening 1272 to receive the colonoscope. Secured to the exterior of fitting 270 and extending through opening 1272 is a short section (a few inches long) of PVP coated, polyurethane liner 1274. The free end 1276 of section 1274 is gathered closed with an elastic band 1278 wrapped around end 1276.

With fitting 1270 in place on nozzle 1204, colonoscope 1242 is inserted through liner section 1274, and the tip of the colonoscope is forced through the gathered opening at the free end 1276 of liner section 1274. Then, water is reintroduced through opening 1222 in nozzle 1204 and into liner tube 1262 to re-lubricate the liner. The gathered free end 1276 prevents water from leaking out around colonoscope 1242, and fitting 1270 (which engages the O-ring seal 1219 on nozzle 1204) prevents water from escaping from nozzle 1204.

The water fills liner tube 1262 in the colon, reactivating the lubricous PVP coating and easing the insertion of colonoscope 1242. When the colonoscope is fully inserted so that cecum 1259 is visible, the colonoscope tip is used to push the noneverted free end 1230 of liner 1039 (FIG. 33) through the ileocecal valve. The tip of the colonoscope is then withdrawn back through the cecum and additional water in injected into nozzle 1204 to evert the remainder of liner 1039 into the ileum and beyond. The water is then drained from port 1222 and colonoscope 1242 is reinserted through the ileocecal valve and into the small intestine. Passage of the colonoscope is facilitated by the presence of the lubricous liner.

Besides ensuring that the entire length of liner tube 1262 has a low coefficient of friction during the insertion of colonoscope 1242, the water within tube 1262 (even though at low pressure, such as one to two psi) helps straighten out bends in the colon. This further assists in colonoscope insertion. Although the bends could be straightened even further by increasing the water pressure, care should be taken not to pressurize the water so much as to stretch the colon. A good maximum water pressure is about 4 psi.

Still other embodiments are within the following claims.

What is claimed is:

1. A method for inserting an instrument into the large intestine of a mammal, comprising
emplacing at least a portion of a flexible liner to form within the intestine an inner tube within an outer tube, said inner tube defining a lumen lying within the intestine and having a distal end accessible via the anal opening from outside the body of the mammal, and during emplacing, preventing said instrument from entering said lumen more than an insubstantial amount, and
thereafter passing said instrument into the intestine throuqh said lumen via its said distal end and causing a portion of said instrument to pass beyond a proximal end of said lumen.

2. The method of claim 1 wherein said flexible liner is emplaced by eversion.

3. The method of claim 2 wherein said eversion is achieved by
   folding one end of said liner back upon itself to form said inner and outer tubes connected along an annular fold, and
   introducing said fold into the anal opening.

4. The method of claim 1 further comprising pressurizing a space enclosed between said inner and outer tubes.

5. The method of claim 4 in which said space is pressurized at pressures no greater than 10 pounds per square inch.

6. The method of claim 5 in which said space is pressurized at pressures less than 3 pounds per square inch.

7. The method of claim 1 in which said inner and outer tubes are collapsed against each other prior to said instrument being passed into said lumen.

8. The method of claim 7 wherein said tubes are collapsed by reducing pressure in the space enclosed between said tubes.

9. The method of claim 1 further comprising passing a proximal tip of said instrument through said lumen and beyond a proximal end of said emplaced flexible liner.

10. The method of claim 1 wherein, prior to the emplacing step, said inner tube is at least partially gathered on a storage device, and during emplacing the withdrawal of portions of said liner from said storage device is aided by applying mechanical force to said inner liner to free it from said storage device.

11. The method of claim 10 wherein said mechanically applied force is applied only intermittently.

12. The method of claim 9 wherein a space between said inner tube and said outer tube is subjected to varying pressure in coordination with said intermittently applied mechanical force.

13. The method of claim 12 wherein said pressure is decreased when said mechanical force is being applied.

14. The method of claim 10 wherein said storage device comprises an internal passage and an external wall supporting said liner, and said force is mechanically applied by means of a tool passed via said storage device passage.

15. The method of claim 10 wherein said storage device comprises an internal passage and an external wall supporting said liner, and said force is mechanically applied by inflating a balloon against a wall of said liner.

16. Apparatus for inserting an instrument into the large intestine of a mammal, comprising
   an elongate evertible liner,
   a liner support chamber having a proximal port and a distal port,
   opposite ends of said liner being attached respectively to said ports,
   at least a portion of said liner being gathered in the space between said ports,
   said liner defining a lumen between said ports,
   a rigid guide tube lying within said lumen and between said ports to provide an unobstructed passage for said instrument within at least a portion of said lumen, a portion of said liner being gathered along and supported by an outside wall of said guide tube, and
   a mechanism located in the vicinity of one end of the guide tube for contacting the liner and aiding withdrawal of the liner from the guide tube.

17. The apparatus of claim 16 wherein said mechanism comprises a roller whose outer surface contacts the liner and a support for the roller, the support having a structure for permitting the roller to turn when the liner is being withdrawn from the guide tube, while resisting the turning of the roller when the liner is being moved in the opposite direction.

18. Apparatus for inserting an instrument into the large intestine of a mammal, comprising
   an elongate evertible liner,
   a liner support chamber having a proximal port and a distal port,
   said liner having its two ends attached respectively at said ports,
   a pressurizer for increasing a pressure within said chamber to cause said liner to be everted,
   said liner comprising a material characterized by having a wall thickness to diameter ratio and a zero strain elasticity modulus whose product is less than 4.0 lb/inch$^2$ and a wall thickness to diameter ratio and a 100% strain modulus of elasticity whose product is greater than 0.5 lb/inch$^2$, and
   a walled passage connected to said distal port for bridging a distance from said distal port to the anal sphincter of the mammal, said walled passage having walls made of a pliable material.

19. A method for inserting an instrument into the large intestine of a mammal, comprising
   emplacing at least a portion of a flexible liner to form within the intestine an inner tube within an outer tube, said inner tube defining a lumen lying within the intestine and having a distal end accessible via the anal opening from outside the body of the mammal, said emplacing proceeding without passing said instrument substantially into said intestine, and
   only thereafter passing said instrument substantially into the intestine through said lumen via its said distal end.

20. Apparatus for emplacing a flexible liner into a body cavity, comprising
   a housing for storing the liner in a chamber thereof, said housing comprising a port through which said liner passes during emplacement,
   a guide member disposed within said housing, said guide member having an exterior surface adapted to have the liner at least partially gathered thereon,
   said guide member being adapted to receive fluid and apply said fluid between said exterior surface and said liner to aid in removal of said liner from said guide member during emplacement,
   said housing being adapted to receive fluid in said chamber to cause said liner to be withdrawn from said member and advanced out of said port into the body cavity by everting said liner,
   said guide member comprising a hollow tube for receiving said fluid, an aperture being disposed in a wall of said tube for coupling said fluid from the hollow tube to said exterior surface, said tube tapering from a first diameter at a first end thereof to a reduced diameter at a second end thereof adjacent to said port.

21. The apparatus of claim 20 wherein said tube is removable from said housing at an end opposite to said port.

22. Apparatus for inserting a liner into a body cavity, comprising
- a housing for storing said liner,
- an inserter to which said housing is mounted and adapted to be disposed adjacent to the body cavity during insertion of said liner, said inserter being adapted to attach to and end of the liner and having an inlet for receiving fluid,
- said housing including a member that is adapted to have the liner gathered thereon, said member comprising a hollow tube having an end that includes an inlet for receiving fluid from said inserter inlet,
- said hollow tube including a slot in a wall thereof that provides a path for said fluid to flow from the inlet of said hollow tube out of said hollow tube to urge said liner off of said tube during said insertion and cause said liner to be withdrawn from said housing and advanced by eversion into said body cavity,
- said housing being removable from said inserter, whereby after said liner is inserted into the body cavity and said housing is removed an instrument can be inserted directly through said inserter and into the body cavity through said liner.

23. Apparatus for inserting a liner into a body cavity, comprising
- a housing for storing said liner,
- an inserter to which said housing is mounted and adapted to be disposed adjacent to the body cavity during insertion of said liner, said inserter being adapted to attach to an end of the liner,
- an inlet in said inserter for receiving fluid to cause said liner to be withdrawn from said housing and advanced by eversion into said body cavity,
- said housing being removable from said inserter, whereby after said liner is inserted into the body cavity and said housing is removed an instrument can be inserted directly through said inserter and into the body cavity through said liner,
- a fitting adapted to be secured to said inserter in place of said housing and to receive said instrument, said fitting being substantially fluid-tight so that as said instrument is inserted fluid that is disposed within said liner is inhibited from escaping through said inserter, said fitting comprising
- a port for receiving said instrument, and
- a tube disposed within said inserter when said fitting is in place on said inserter, said tube having a first, open end secured to said fitting in communication with said port, and a second end adapted to fit snugly around said instrument when said instrument is inserted therethrough via said port to inhibit said fluid from escaping through said second end.

24. The apparatus of claim 23 wherein said tube includes a band of elastic material disposed around said second end.

25. Apparatus for inserting an instrument into the large intestine of a mammal, comprising
- an elongate evertible liner,
- a liner support chamber having a proximal port and a distal port,
- opposite ends of said liner being attached respectively to said ports,
- at least a portion of said liner being gathered in the space between said ports,
- said liner defining a lumen between said ports,
- a rigid guide tube lying within said lumen and between said ports to provide an unobstructed passage for said instrument within at least a portion of said lumen, and
- a walled passage connected to said distal port for bridging a distance from said distal port to the anal sphincter of a human, said walled passage having walls made of a pliable material.

26. Apparatus for inserting an instrument into the intestine of a mammal, comprising
- an elongate evertible liner,
- a liner support chamber,
- said chamber having a distal port and a proximal port,
- a tube extending distally from said distal port,
- said liner having its opposite ends attached respectively to said ports,
- the end of said liner attached to said distal port being everted over and gathered along said tube,
- a pressurizer for increasing the pressure within said liner during eversion to aid the gathered portion of said liner to slide along and be released from said tube, and
- a walled passage connected to said distal port for bridging a distance from said distal port to the anal sphincter of a human, said walled passage having walls made of a pliable material.

* * * * *

UNITED STATES PATENT AND TRADEMARK OFFICE
CERTIFICATE OF CORRECTION

PATENT NO. : 5,236,423

DATED : August 17, 1993

INVENTOR(S) : Thomas W. Mix et al.

It is certified that error appears in the above-identified patent and that said Letters Patent are hereby corrected as shown below:

Col. 9, line 57, "t" should be --to--.

Col. 15, line 31, "wet," should be --wet.--

Col. 20, line 29, "110" should be --1101--.

Col. 21, line 42, "103" should be --1039--.

Col. 23, line 14, "Within" should be --within--;
line 24, "262" should be --1262--.

Col. 24, line 3, "Cases" should be --cases--;
line 8, "Way" should be --way--.

Col. 25, line 36, "9" should be --11--.

Signed and Sealed this

Fifteenth Day of March, 1994

Attest:

BRUCE LEHMAN

*Attesting Officer*     *Commissioner of Patents and Trademarks*